US010384151B2

(12) United States Patent
Liu et al.

(10) Patent No.: US 10,384,151 B2
(45) Date of Patent: Aug. 20, 2019

(54) HIGH PRESSURE VALVE WITH TWO-PIECE STATOR ASSEMBLY

(71) Applicant: IDEX Health & Science LLC, Oak Harbor, WA (US)

(72) Inventors: Quan Liu, Petaluma, CA (US); Jeremy Hayes, Santa Rosa, CA (US)

(73) Assignee: IDEX Health & Science LLC, Oak Harbor, WA (US)

( * ) Notice: Subject to any disclaimer, the term of this patent is extended or adjusted under 35 U.S.C. 154(b) by 1 day.

(21) Appl. No.: 15/373,584

(22) Filed: Dec. 9, 2016

(65) Prior Publication Data

US 2018/0161697 A1 Jun. 14, 2018

(51) Int. Cl.
| | |
|---|---|
| *B01D 15/22* | (2006.01) |
| *G01N 30/20* | (2006.01) |
| *F16K 11/074* | (2006.01) |
| *F16K 31/04* | (2006.01) |
| *G01N 30/22* | (2006.01) |

(52) U.S. Cl.
CPC .......... *B01D 15/22* (2013.01); *F16K 11/0743* (2013.01); *G01N 30/20* (2013.01); *F16K 11/074* (2013.01); *F16K 31/041* (2013.01); *G01N 30/22* (2013.01); *G01N 2030/201* (2013.01); *G01N 2030/202* (2013.01); *G01N 2030/207* (2013.01)

(58) Field of Classification Search
CPC ..... B01D 15/22; F16K 31/041; F16K 11/074; G01N 30/20; G01N 30/201; G01N 2030/207
See application file for complete search history.

(56) References Cited

U.S. PATENT DOCUMENTS

| | | | |
|---|---|---|---|
| 3,494,175 A | 2/1970 | Cusick et al. | |
| 3,752,167 A | 8/1973 | Makabe | |
| 3,868,970 A | 3/1975 | Ayers et al. | |
| 4,242,909 A | 1/1981 | Gundelfinger | |
| 4,243,071 A | 1/1981 | Shackelford | |
| 4,444,066 A * | 4/1984 | Ogle ..................... | G01N 30/20 73/61.56 |
| 4,705,627 A | 11/1987 | Miaw et al. | |

(Continued)

FOREIGN PATENT DOCUMENTS

| | | |
|---|---|---|
| DE | 3502847 | 7/1986 |
| EP | 2564104 | 3/2013 |

OTHER PUBLICATIONS

ISR and Written Opinion, PCT/US2017/65293, dated Dec. 8, 2017.

*Primary Examiner* — Matthew W Jellett
*Assistant Examiner* — Christopher D Ballman
(74) *Attorney, Agent, or Firm* — Vinson & Elkins, L.L.P.

(57) ABSTRACT

Valve with two-piece stator assembly for use with liquid chromatography or other analytical systems. A separate and removable stator plate is provided with a mounting device to provide a two-piece stator assembly. The mounting device is adapted on one side to engage and contact the stator plate, and on the other side includes a plurality of ports for fluidic connections which are in fluid communication with fluid passageways in the stator plate. By making the stator face a separate component, the overall costs of the valve can be reduced, different materials can be used for the mounting device and the stator, and the valve can be used for ultra-high pressure applications, including in liquid chromatography and other analytical instrument systems.

38 Claims, 23 Drawing Sheets

(56) References Cited

U.S. PATENT DOCUMENTS

| | | |
|---|---|---|
| 4,722,830 A | 2/1988 | Urie et al. |
| 5,193,581 A | 3/1993 | Shiroto et al. |
| 5,419,419 A | 5/1995 | Macpherson |
| 5,525,303 A | 6/1996 | Ford et al. |
| 5,730,943 A | 3/1998 | Ford et al. |
| 6,056,331 A | 5/2000 | Benett et al. |
| 6,095,572 A | 8/2000 | Ford et al. |
| 6,267,143 B1 * | 7/2001 | Schick .................. G01N 30/20 137/625.11 |
| 7,308,908 B2 * | 12/2007 | Keene .................... F16K 11/07 137/554 |
| 7,311,502 B2 | 12/2007 | Gerhardt et al. |
| 7,811,452 B2 | 10/2010 | Yin et al. |
| 8,071,052 B2 | 12/2011 | Baeuerle et al. |
| 8,696,038 B2 | 4/2014 | Nienhuis |
| 8,905,075 B2 * | 12/2014 | Tower ...................... F16K 3/08 137/625.15 |
| 9,234,608 B2 * | 1/2016 | Stearns ................. F16K 49/002 |
| 2003/0196700 A1 * | 10/2003 | Gilbert ...................... F16K 3/08 137/375 |
| 2005/0127097 A1 | 6/2005 | Straka et al. |
| 2005/0269264 A1 | 12/2005 | Fermier et al. |
| 2007/0283746 A1 | 12/2007 | Gerhardt et al. |
| 2009/0321356 A1 | 12/2009 | Gerhardt et al. |
| 2010/0171055 A1 * | 7/2010 | Dourdeville .......... B23K 20/023 251/129.11 |
| 2011/0233440 A1 * | 9/2011 | Gamache ................ F16K 11/20 251/319 |
| 2011/0303304 A1 * | 12/2011 | Tower ...................... F16K 3/08 137/269 |
| 2012/0024411 A1 | 2/2012 | Hahn et al. |
| 2012/0061955 A1 | 3/2012 | Hochgraeber et al. |
| 2013/0043677 A1 | 2/2013 | Gibson |
| 2013/0284959 A1 | 10/2013 | Hochgraeber et al. |
| 2014/0042349 A1 * | 2/2014 | Wiechers ............... G01N 30/26 251/129.11 |
| 2016/0082439 A1 * | 3/2016 | Servin .................... B01L 3/567 422/538 |
| 2016/0116088 A1 | 4/2016 | Graham et al. |

* cited by examiner

SECTION A-A

SECTION B-B

HIGH PRESSURE VALVE WITH TWO-PIECE STATOR ASSEMBLY

1. FIELD OF THE INVENTION

The present disclosure relates generally to valves such as those used in liquid chromatography systems and other analytical instrument systems.

2. BACKGROUND OF THE INVENTION

Liquid chromatography (LC) is a well-known technique for separating the constituent elements in a given sample. In a conventional LC system, a liquid solvent (referred to as the "mobile phase") is introduced from a reservoir and is pumped through the LC system. The mobile phase exits the pump under pressure. The mobile phase then travels via tubing to a sample injection valve. As the name suggests, the sample injection valve allows an operator to inject a sample into the LC system, where the sample will be carried along with the mobile phase.

In a conventional LC system, the sample and mobile phase pass through one or more filters and often a guard column before coming to the column. A typical column usually consists of a piece of steel tubing which has been packed with a "packing" material. The "packing" consists of the particulate material "packed" inside the column. It usually consists of silica- or polymer-based particles, which are often chemically bonded with a chemical functionality. The packing material is also known as the stationary phase. One of the fundamental principles of separation is the mobile phase continuously passing through the stationary phase. When the sample is carried through the column (along with the mobile phase), the various components (solutes) in the sample migrate through the packing within the column at different rates (i.e., there is differential migration of the solutes). In other words, the various components in a sample will move through the column at different rates. Because of the different rates of movement, the components gradually separate as they move through the column. Differential migration is affected by factors such as the composition of the mobile phase, the composition of the stationary phase (i.e., the material with which the column is "packed"), and the temperature at which the separation takes place. Thus, such factors will influence the separation of the sample's various components.

Once the sample (with its components now separated) leaves the column, it flows with the mobile phase past a detector. The detector detects the presence of specific molecules or compounds. Two general types of detectors are used in LC applications. One type measures a change in some overall physical property of the mobile phase and the sample (such as their refractive index). The other type measures only some property of the sample (such as the absorption of ultraviolet radiation). In essence, a typical detector in a LC system can measure and provide an output in terms of mass per unit of volume (such as grams per milliliter) or mass per unit of time (such as grams per second) of the sample's components. From such an output signal, a "chromatogram" can be provided; the chromatogram can then be used by an operator to determine the chemical components present in the sample.

In addition to the above components, a LC system will often include filters, check valves, a guard column, or the like in order to prevent contamination of the sample or damage to the LC system. For example, an inlet solvent filter may be used to filter out particles from the solvent (or mobile phase) before it reaches the pump. A guard column is often placed before the analytical or preparative column; i.e., the primary column. The purpose of such a guard column is to "guard" the primary column by absorbing unwanted sample components that might otherwise bind irreversibly to the analytical or preparative column.

In practice, various components in an LC system may be connected by an operator to perform a given task. For example, an operator will select an appropriate mobile phase and column, then connect a supply of the selected mobile phase and a selected column to the LC system before operation. In order to be suitable for high performance liquid chromatography (HPLC) applications, each connection must be able to withstand the typical operating pressures of the HPLC system. If the connection is too weak, it may leak. A leakage will definitely result in an unsuccessful or inaccurate analysis, such as inconsistent results or a total loss of the sample to be analyzed. Because the types of solvents that are sometimes used as the mobile phase are often toxic and because it is often expensive to obtain and/or prepare many samples for use, any such connection failure is a serious concern.

It is fairly common for an operator to disconnect a column (or other component) from a LC system and then connect a different column (or other component) in its place after one test has finished and before the next begins. Given the importance of leak-proof connections, especially in HPLC applications, the operator must take time to be sure the connection is sufficient. Replacing a column (or other component) may occur several times in a day. Moreover, the time involved in disconnecting and then connecting a column (or other component) is unproductive because the LC system is not in use and the operator is engaged in plumbing the system instead of preparing samples or other more productive activities. Hence, the replacement of a column in a conventional LC system involves a great deal of wasted time and inefficiencies.

Given concerns about the need for leak-free connections, conventional connections have been made with stainless steel tubing and stainless steel end fittings. More recently, however, it has been realized that the use of stainless steel components in a LC system have potential drawbacks in situations involving biological samples. For example, the components in a sample may attach themselves to the wall of stainless steel tubing. This presents problems because the detector's measurements (and thus the chromatogram) of a given sample may not accurately reflect the sample if some of the sample's components or ions remain in the tubing, and do not pass the detector. Perhaps of even greater concern, however, is the fact that ions from the stainless steel tubing may detach from the tubing and flow past the detector, thus leading to potentially erroneous results. Additionally, ions can easily bind to biological compounds of interest, resulting in changes to the molecules that affect their retention time in the column. Hence, there is a need for "biocompatible" connections through the use of a material that is chemically inert with respect to such "biological" samples and the mobile phase used with such samples so that ions will not be released by the tubing and thus contaminate the sample.

Multiport selector/injector valves are well known and have been used in a variety of industrial processes, such as liquid chromatography and mass spectrometry. For example, selection valves are commonly used in liquid chromatography and other analytical methods to direct fluid flow along alternate paths. Such valves are also used to terminate fluid withdrawal from one source and select another source of fluid, for example, such as when a variety of streams in an industrial process is selectively sampled for analysis.

Injector/selector valves are often used in high pressure liquid chromatography (HPLC) or gas chromatography (GC). U.S. Pat. No. 4,242,909 (Gundelfinger '909), which is hereby fully incorporated by reference, describes sample injection apparatus for withdrawing liquid samples from vials and injecting them into a chromatographic column or other analyzing device. The apparatus is said to minimize wastage, cross contamination, and dilution of the samples, and to be capable of automation with a minimum of complexity. Injector/selector valves are particularly useful in chromatographic applications since a substantial amount of time and effort is required to set up a particular HPLC or GC system, which may often utilize multiple columns and/or multiple detection systems. Multiport selection valves permit the operator of the chromatograph to redirect flows such that particular samples are selected for injection into a particular column, or alternatively, to direct the output from a particular column to one or more different detectors.

As mentioned above, multiport selection valves have been known for some time, including those which utilize a cylindrical rotor and stator combination. In some of these valves, the stator holds the fluid tubes in fixed relation to each other and presents the tube ends to a rotor face which may contain a grooved surface. By varying the angle of the rotor, the tubes are selectively brought into fluid communication. One type of injector/selector valve using a rotor/stator combination is the Type 50 rotary valve from Rheodyne, Incorporated. The Type 50 valves are said to operate by rotation of a flat rotor against a flat stator (see "Operating Instructions for Type 50 Teflon Rotary Valves," Rheodyne, Incorporated, printed in U.S.A. April 1994). Another rotor/stator selector valve is shown in U.S. Pat. No. 5,193,581 (Shiroto, et al.), which is hereby fully incorporated by reference. The valve is said to comprise, among other things, a stator plate having a plurality of outlet holes extending through the stator plate and arranged in a circle concentric with a valve casing, and a rotor having a U-shaped passage formed in the rotor. The rotor is said to be rotated through a desired angle so that an inlet hole can be in fluid communication with selected ones of the outlet holes through the U-shaped passage of the rotor.

U.S. Pat. No. 5,419,419 (Macpherson) describes a rotary selector valve that is used in connection with an automatic transmission in an automobile. A motor is said to index a shear plate of the selector valve to predetermined positions for shifting the transmission. A series of working lines as shown in FIG. 6 are maintained in a closed spatial relationship with the casing.

U.S. Pat. No. 3,494,175 (Cusick, et al.) discloses a valve having a plurality of capillaries which are held in spaced relationship within a manifold plate member. U.S. Pat. No. 3,752,167 (Makabe) discloses a fluid switching device including a plurality of capillaries that are held within threaded holes by couplings. A rotary member allows fluid communication between the tubes. U.S. Pat. No. 3,868,970 (Ayers, et al.) discloses a multipositional selector valve said to be adapted with a means for attaching a plurality of chromatographic columns to the valve, such that the flow can be directed into any of the columns. U.S. Pat. No. 4,705,627 (Miwa, et al.) discloses a rotary valve said to consist of two stator discs and a rotor disposed between the two stator discs. Each time the rotor is turned intermittently it is said, different passages are formed through which the fluid in the valve runs. U.S. Pat. No. 4,722,830 (Urie, et al.) discloses multiport valves. The multiport valves are said to be used in extracting fluid samples from sample loops connected with various process streams.

In many applications using selector/injector valves to direct fluid flows, and in particular in liquid and gas chromatography, the volume of fluids is small. This is particularly true when liquid or gas chromatography is being used as an analytical method as opposed to a preparative method. Such methods often use capillary columns and are generally referred to as capillary chromatography. In capillary chromatography, both gas phase and liquid phase, it is often desired to minimize the volume of the fluid flowpath (e.g., length and/or size of the fluid pathways) of the valve. One reason for this is that a valve having a larger volume for the fluid flowpath will contain a relatively larger volume of liquid, and when a sample is injected into the valve the sample will be diluted, decreasing the resolution and sensitivity of the analytical method, and may result in a dead volume being introduced into the fluid pathway.

Micro-fluidic analytical processes also involve small sample sizes. As used herein, sample volumes considered to involve micro-fluidic techniques can range from as low as volumes of only several picoliters or so, up to volumes of several milliliters or so, whereas more traditional LC techniques, for example, historically often involved samples of about one microliter to about 100 milliliters in volume. Thus, the micro-fluidic techniques described herein involve volumes one or more orders of magnitude smaller in size than traditional LC techniques. Micro-fluidic techniques can also be expressed as those involving fluid flow rates of about 0.5 ml/minute or less.

Most conventional HPLC systems include pumps which can generate relatively high pressures of up to around 5,000 psi to 9,000 psi or so. In many situations, an operator can obtain successful results by operating a LC system at "low" pressures of anywhere from just a few psi or so up to 1,000 psi or so. More often than not, however, an operator will find it desirable to operate a LC system at relatively "higher" pressures of over 1,000 psi.

Another, relatively newer liquid chromatography form is Ultra High Performance Liquid Chromatography (UHPLC) in which system pressure extends upward to about 1400 bar or 20,000 psi or so, or even more. In order to achieve greater chromatographic resolution and higher sample throughput, the particle size of the stationary phase has become extremely small. A stationary phase particle as small as 1 micron is common; the resulting high column packing density leads to substantially increased system pressure at the head of the column. Both HPLC and UHPLC are examples of analytical instrumentation that utilize fluid transfer at elevated pressures. For example, in U.S. Patent Publication No. 2007/0283746 A1, published on Dec. 13, 2007 and titled "Sample Injector System for Liquid Chromatography," an injection system is described for use with UHPLC applications, which are said to involve pressures in the range from 20,000 psi to 120,000 psi. In U.S. Pat. No. 7,311,502, issued on Dec. 25, 2007 to Gerhardt, et al., and titled "Method for Using a Hydraulic Amplifier Pump in Ultrahigh Pressure Liquid Chromatography," the use of a hydraulic amplifier is described for use in UHPLC systems involving pressures in excess of 25,000 psi. In U.S. Patent Publication No. 2005/0269264 A1, published on Dec. 8, 2005 and titled "Chromatography System with Gradient Storage and Method for Operating the Same," a system for performing UHPLC is disclosed, with UHPLC described as involving pressures above 5,000 psi (and up to 60,000 psi). Applicants hereby incorporate by reference as if fully set forth herein U.S. Pat. No. 7,311,502 and US Patent Publications Nos. 2007/0283746 A1 and 2005/0269264 A1.

As noted, liquid chromatography (as well as other analytical) systems, including HPLC or UHPLC systems, typically include several components. For example, such a system may include a pump; an injection valve or autosampler for injecting the analyte; a precolumn filter to remove particulate matter in the analyte solution that might clog the column; a packed bed to retain irreversibly adsorbed chemical material; the HPLC column itself; and a detector that analyzes the carrier fluid as it leaves the column. These various components may typically be connected by a miniature fluid conduit, or tubing, such as metallic or polymeric tubing, usually having an internal diameter of 0.001 to 0.040 inch.

All of these various components and lengths of tubing are typically interconnected by threaded fittings. Fittings for connecting various LC system components and lengths of tubing are disclosed in prior patents, for example, U.S. Pat. Nos. 5,525,303; 5,730,943; and 6,095,572, the disclosures of which are herein all incorporated by reference as if fully set forth herein. Often, a first internally threaded fitting seals to a first component with a ferrule or similar sealing device. The first fitting is threadedly connected through multiple turns by hand or by use of a wrench or wrenches to a second fitting having a corresponding external fitting, which is in turn sealed to a second component by a ferrule or other seal. Disconnecting these fittings for component replacement, maintenance, or reconfiguration often requires the use of a wrench or wrenches to unthread the fittings. Although a wrench or wrenches may be used, other tools such as pliers or other gripping and holding tools are sometimes used. It will be understood by those skilled in the art that, as used herein, the term "LC system" is intended in its broad sense to include all apparatus and components in a system used in connection with liquid chromatography, whether made of only a few simple components or made of numerous, sophisticated components which are computer controlled or the like. Those skilled in the art will also appreciate that an LC system is one type of an analytical instrument (AI) system. For example, gas chromatography is similar in many respects to liquid chromatography, but obviously involves a volatile sample to be analyzed, and uses a gas as a mobile phase. Such analytical instrument systems include high performance or high pressure liquid chromatography systems, an ultra high performance or ultra high pressure liquid chromatography system, a mass spectrometry system, a microflow chromatography system, a nanoflow chromatography system, a nano-scale chromatography system, a capillary electrophoresis system, a reverse-phase gradient chromatography system, or a combination thereof. Although the following discussion focuses on liquid chromatography, those skilled in the art will appreciate that much of what is said also has application to other types of AI systems and methods.

Increasing pressure requirements in liquid chromatography have necessitated the use of high pressure fluidic components. For many applications regular stainless steel tubing can be used to withstand the high pressure. However, for some types of analyses (e.g., biological testing and metal/ion analysis), stainless steel or other metals are not desired in the fluid path as the metal could interfere with the testing. Additionally, there are some fields of use (e.g., nano-scale or nano-volume analysis), that require very small inside diameters to accommodate the extremely low volumes required by these applications. Such small inside diameters are typically not available in stainless steel or other high pressure tubing.

In high-performance liquid chromatography (HPLC), ultra high-performance liquid chromatography (UHPLC), and other high-pressure analytic chemistry applications, various system components and their fluidic connections must be able to withstand pressures of 15,000 to 20,000 psi or so. The types of fluidic connection systems between the tubes that carry fluids and the ports that receive fluids in these high-pressure applications are limited. Many fluidic connection systems rely on cone-shaped, threaded, or welded fittings to attach a tube to a receiving port. These types of connections sometimes may have drawbacks, however. For example, the size of cone-shaped fittings and threaded fittings are dependent on the type and size of any given port, which makes quickly interchanging a tube fitted with a particular cone or threaded fitting between various ports difficult. Other compression-based fittings have been employed to address this problem. Such fittings often employ a ferrule or a lock ring to help secure one end of a tube to a receiving port. However, ferrules and lock rings can become deformed after multiple uses (e.g., by connecting, disconnecting, and reconnecting to various ports). This is especially true in high-pressure applications, where a fluid-tight seal is essential, and where a ferrule or lock ring may be more likely to become deformed in creating such a seal.

For example, published U.S. Patent Application No. 2013/0043677, titled "Tube and Pipe End Cartridge Seal," published on Feb. 21, 2013, describes a tube and pipe end cartridge seal for use at high pressures, which relies on a fitting body (including ferrule fittings) to effectuate a seal with the axial end of a tube. Moreover, a dimple is forged on the annular end of the tube face to further effectuate the seal. Likewise, U.S. Pat. No. 6,056,331, titled "Zero Dead Volume Tube to Surface Seal," issued to Bennett et al. on May 2, 2000, describes an apparatus for connecting a tube to a surface using a body, a ferrule, and a threaded fitting. Although Bennett et al. discloses a type of tube face-sealing apparatus, the apparatus of Bennet et al. relies on a threaded fitting and a ferrule. Similarly, published U.S. Patent Application No. 2012/0061955, titled "Plug Unite and Connection System for Connecting Capillary Tubes, Especially for High-Performance Liquid Chromatography," published on Mar. 15, 2012, discloses a plug unit connection system for capillary tubes, wherein a seal is provided at the interface between a capillary tube and a bushing unit, instead of at the location of a ferrule or conical fitting. However, U.S. Patent Application No. 2012/0061955 relies on the use of a pressure piece similar to a ferrule to ensure that enough axial force can be generated to obtain a seal at the tube face.

Connection assemblies which attempt to effectuate a seal for high-pressure applications can require a significant amount of torque to effectuate a fluid-tight seal, making the creation of such seals difficult without the use of additional tools and increasing the risk of damage to the fitting assembly or its components due to overtightening. Moreover, experience suggests that many users do not like to use various tools to connect or disconnect tubing from components such as those in various AI systems. It is believed that users often apply different amounts of torque to connect or disconnect tubing and the components in such systems, thus resulting in potential problems caused by over-tightening or under-tightening (e.g., leakage or loss of sealing when the fluid is under pressure).

One example of a flat-bottomed or face-sealing connection assembly is provided by U.S. Pat. No. 8,696,038, titled "Flat Bottom Fitting Assembly" and issued on Apr. 15, 2014 to Nienhuis. Nienhuis teaches a type of flat bottom assembly which includes a flat-sided ferrule, and wherein the assembly including the ferrule and the tube can be pressed against a flat bottom port. Another example of a flat-bottomed or face-sealing connection assembly is provided by published U.S. Patent Application No. 2012/0024411, titled "Biocompatible Tubing for Liquid Chromatography Systems," which was published on Feb. 2, 2012 and was filed on behalf of Hahn et al. The Hahn et al. published patent application describes tubing having an inner layer and an outer layer, and in which the inner layer can be biocompatible material such as polyetheretherketone (PEEK) and the outer layer may be a different material, and in which an end of the tubing may be flared or otherwise adapted to have a larger outer diameter than other portions of the tubing. The current state of the art for high pressure connections in both HPLC and UHPLC is to utilize coned ports along with some form of ferrule and nut combination with tubing. The nut translates rotational torque into axial load that is translated to the ferrule. The load causes the ferrule to deform/deflect and grip the tubing, creating a seal. The tube is typically forced into the bottom of the coned port, but there is not currently a mechanism to ensure there is not a gap or space at the port bottom.

The space at the bottom of the port is a concern for those performing liquid chromatography experiments due to the potential to negatively influence the results with carry over and band broadening. Carry over is just as it sounds, analyte from one test is carried over to the next. Carry over can produce very unstable results for obvious reasons. Band broadening is when the peaks identifying a substance become less symmetric and make identification more difficult when peaks of different molecules have similar retention times.

One issue with conventional ferrules used with coned ports is that the torque required to deform/deflect is typically above finger tight levels in order to achieve UHPLC pressures (e.g., above 12,000 psi or so). It is desirable to remove tools from the lab by making them unnecessary for making and breaking fluidic connections and it is advantageous to have fittings that can be connected simply with the fingers rather than tools.

European Patent No. EP 2564104 describes a sealing system for use at high pressure. End-face seals minimize the sealing radius and therefore allow various fittings—including known ferrule fittings—to be used in high-pressure systems. End-face seals at such high pressure may require smooth surfaces, however. In order to reduce cost, an end-face preparation tool may be required to forge a dimple into the end face to mechanically deform and smooth the surface.

U.S. Pat. No. 6,056,331 describes an apparatus that is composed of three components, a body, a ferrule, and a threaded fitting. The ferrule is compressed onto a tube and a seal is formed between the tube and a device retained in the body by threading the fitting into the body which provides pressure that seals the face of the ferrule to a mating surface on the device. This seal may be used at elevated temperatures, depending on the materials used. This fitting was developed for use with micro-machined silicon wafers used in capillary gas chromatography.

In many conventional valves, such as rotary shear valves, a stator member at one end has two or more ports to receive tubing which can be removably attached to provide fluid connections to the valve. Such a stator member typically serves as least two functions: it provides a planar stator face which mates with a rotor seal, and also provides fluid channels or pathways between the ports and the stator face. In typical such valves, the stator member is a single piece and is often designed so that the ports to receive the tubing are oriented at angles with respect to the longitudinal axis of the stator member and the valve generally. This approach is generally due to the need to provide several ports on the end surface of the stator member, as well as several screws or nuts to secure the stator member to the valve body, and the limited size of the stator member and the resulting limited space available for the ports, as well as the need to allow enough space for an operator to connect and disconnect tubing from the ports of the stator member. An example of a valve with such a single-piece stator is described and shown in U.S. Pat. No. 8,905,075 B2, issued on Dec. 9, 2014, to Tower, and entitled "Rotary Shear Valve Assembly with Hard-on-Hard Seal Surfaces," which is hereby incorporated by reference as if fully set forth herein.

While this configuration has worked in the past, and still works for many applications, it also typically requires that the fluid passageways between the ends of the tubing and the stator face are longer and therefore have a greater volume than may be desired. Those skilled in the art will appreciate that the volumes in valves used for analytical science applications generally require very precise control over the volumes of the fluid passageways, and the use of smaller and smaller sample sizes means that the precise control of such volumes can become important. In addition, stator members of this type are often made of metal, such as stainless steel, and the manufacturing and machining of such stator members can be costly and time consuming. The use of angled ports tends to require that the stator member be larger in size, and this also tends to increase the costs of such stator members. In addition to these issues, the alignment of the fluid flowpaths of the components once assembled can be problematic with such conventional stator members. It will be appreciated that the tubing will have an inner diameter through which the fluid flows, and the ports of the stator member will likewise have openings at the bottom of the ports, with those openings providing fluid passageways. If the stator member surface has been lapped during manufacturing, which is often the case, then the openings of the ports may shift in shape, size or location, thereby causing potential difficulties in the alignment of the openings; the alignment of the openings is usually desired in order to prevent turbulent fluid flow.

U.S. Pat. Nos. 3,494,175, 3,752,167, 3,868,970, 4,242,909, 4,705,627, 4,722,830, 5,193,581, 5,419,419, 5,525,303, 5,730,943, 6,056,331, 6,095,572, 7,311,502, 7,811,452, 8,071,052, 8,696,038, European Patent No. EP2564104, and published U.S. Patent Application Nos. 2005/0269264, 2007/0283746, 2009/0321356, 2010/0171055, 2012/0024411, 2012/0061955, 2013/0043677, and 2016/0116088 are hereby incorporated by reference as if fully set forth herein.

SUMMARY OF THE INVENTION

The present disclosure in one embodiment provides a valve with a two-piece stator assembly useful for use with, among other applications, high pressure liquid chromatography or other analytical instrument systems. In one embodiment, a separate and removable stator plate is provided and is adapted to engage with a mounting device to provide a two-piece stator assembly for one end of a valve. The mounting device is adapted on one side to engage and contact one side of the stator plate, and on the other side includes a plurality of ports for receiving a plurality of fitting assemblies for fluidic connections via tubing. The ports of the mounting device are in fluid communication with one or more fluid pathways in the stator plate and/or one or more fluid pathways in a rotor seal located on the second side of the stator plate. By making the stator face a separate and replaceable component distinct from the mounting device, a number of advantages are achieved, including providing greater flexibility for the use of the valve in various applications, reducing the overall costs of the valve, allowing the use of different materials for the mounting device and the stator plate, and others as described below. Although different configurations for the ports of the mounting device and for fitting assemblies used to removably secure tubing in the ports of the mounting device may be used, flat-bottomed ports adapted to removably hold face-sealing fitting assemblies provide advantages (as described in more detail below).

In one embodiment, a high-pressure valve for liquid chromatography is provided comprising a mounting plate having a first side and a second side, and having a plurality of openings therethrough, wherein each of the plurality of openings is adapted to removably receive tubing in the first side of said mounting plate, as well as a stator plate having a first side and a second side, wherein the first side of said stator plate is adapted to engage with the second side of said mounting plate, wherein said stator plate has a plurality of openings in the first side and second side of said stator plate, and at least a plurality of the openings in the second side of said mounting plate are in fluid communication with corresponding openings in the first side of said stator plate, and wherein said stator plate and said mounting plate are removably attached to one another. The valve also includes a rotor seal adapted to engage with at least one of the first side and second side of said stator plate, a rotor shaft which is rotatable around a longitudinal axis, and a housing within which the rotor seal and at least a portion of said rotor shaft are located, wherein said mounting plate and said stator plate are removably attached to said housing. The valve may have a mounting plate which comprises a first material and a stator plate which comprises a second material. The stator plate can comprise a metal, a biocompatible material, and/or a ceramic material, or a combination thereof. The plurality of openings in said mounting plate can further comprise flat-bottomed ports for removably receiving tubing, and the first side of said stator plate can further comprise bosses aligned to extend partially into the bottom of the ports of said mounting plate. The stator plate may comprise a plurality of layers bonded together, such as by diffusion bonding. The mounting plate may comprise one or more of aluminum, copper, steel, stainless steel, titanium, polyetheretherketone, polypropylene, polysulfone, DELRIN, ULTEM, polyphenylen sulfide (PPS), polytetrafluoroethylene, nylon, polyamides, or a combination thereof. The stator plate also may comprise a plurality of layers bonded together, such as by diffusion bonding, wherein at least one of said layers comprises one or more of stainless steel, titanium, MP35N, ceramics, glass, or a combination thereof. In some embodiments, the stator plate may further comprise a guide layer, wherein the guide layer comprises openings with a greater width than the openings of the layer below the guide layer and the guide layer is adapted to be adjacent to the second side of said mounting plate. In addition, the stator plate can be designed and adapted to be removable from said mounting device and the valve. A valve according to the present disclosure can be adapted to operate with fluid pressures of a fluid flowing therethrough of at least 1,000 psi, 5,000 psi, 10,000 psi, 15,000 psi, 20,000 psi, and/or 25,000 psi.

In one embodiment, a removable stator plate for a high-pressure valve for an analytical instrument system is provided, wherein said stator plate comprises a first side, a second side, with each of the first side and the second side having a plurality of openings, and a plurality of passageways therethrough wherein each of the passageways provides fluid communication between at least one opening on the first side and at least one opening on the second side of said stator plate, and wherein said stator plate comprises a plurality of layers bonded together by diffusion bonding, and wherein the first side of said stator plate is adapted to sealingly engage with one side of a mounting plate, which is adapted to receive and sealingly hold a plurality of tubes, and the second side of said stator plate is adapted to sealingly engage with one side of a rotor seal of a valve, and said stator plate and said mounting plate are adapted to be removably attached to a body of a valve. The stator plate may comprise one or more biocompatible materials, and may comprise four layers, with at least two layers bonded together by diffusion bonding. In one embodiment, the first side of said stator plate may comprise at least four openings and at least two passageways therethrough. The stator plate may also further comprise one or more of the following analytical instrument system: a sample loop, a mixing element, a column, a filter, a heating element, a sensor, or a detector. The stator plate may be adapted to be removed from a valve and replaced by a second stator plate, wherein said second stator plate comprises a different material than said stator plate, and/or the stator plate may be adapted to be removed from a valve and replaced by a second stator plate, wherein said second stator plate comprises one or more different analytical instrument system elements than said stator plate.

In another embodiment, an analytical instrument (AI) system, such as a liquid chromatography system, is provided which comprises a valve comprising (a) a mounting plate having a first side and a second side, and having a plurality of openings therethrough, wherein each of the plurality of openings is adapted to removably receive tubing in the first side of said mounting plate, and (b) a stator plate having a first side and a second side, wherein the first side of said stator plate is adapted to engage with the second side of said mounting plate, wherein said stator plate has a plurality of openings in the first side and second side of said stator plate, and at least a plurality of the openings in the second side of said mounting plate are in fluid communication with corresponding openings in the first side of said stator plate, and wherein said stator plate and said mounting plate are removably attached to one another. The AI system may have a stator plate and a mounting plate which are adapted to be removably attached to one another, the valve may be adapted to operate with fluid pressures of at least 1,000 psi, 5,000 psi, 10,000 psi, 15,000 psi, 20,000 psi, or 25,000 psi.

In yet another embodiment of the present disclosure, a stator assembly for a high-pressure valve is described that comprises a mounting plate having a first side and a second side, and having a plurality of openings therethrough, wherein the first side of each of the plurality of openings is located in the first side of said mounting plate and is adapted to removably receive tubing therein, and a stator plate having a first side and a second side, wherein the first side of said stator plate and the second side of said mounting plate are adapted to sealingly engage with one another, wherein said stator plate has a plurality of openings in the first side and second side of said stator plate, and at least a plurality of the openings in the second side of said mounting plate are in fluid communication with corresponding openings in the first side of said stator plate, and wherein said mounting plate and said stator plate are adapted to be removably attached to one another. The stator assembly may have the plurality of openings in the second side of the mounting plate and the corresponding openings in the first side of said stator plate aligned with one another.

In still another embodiment, methods of use and operation of a valve with a removable and replaceable stator plate are described, involving the disassembly of a valve having a stator plate, removing a first stator plate and replacing it with a second stator plate, then reassembling the valve by reattaching the second stator plate and the mounting device to the valve.

DETAILED DESCRIPTION

Figure 1:
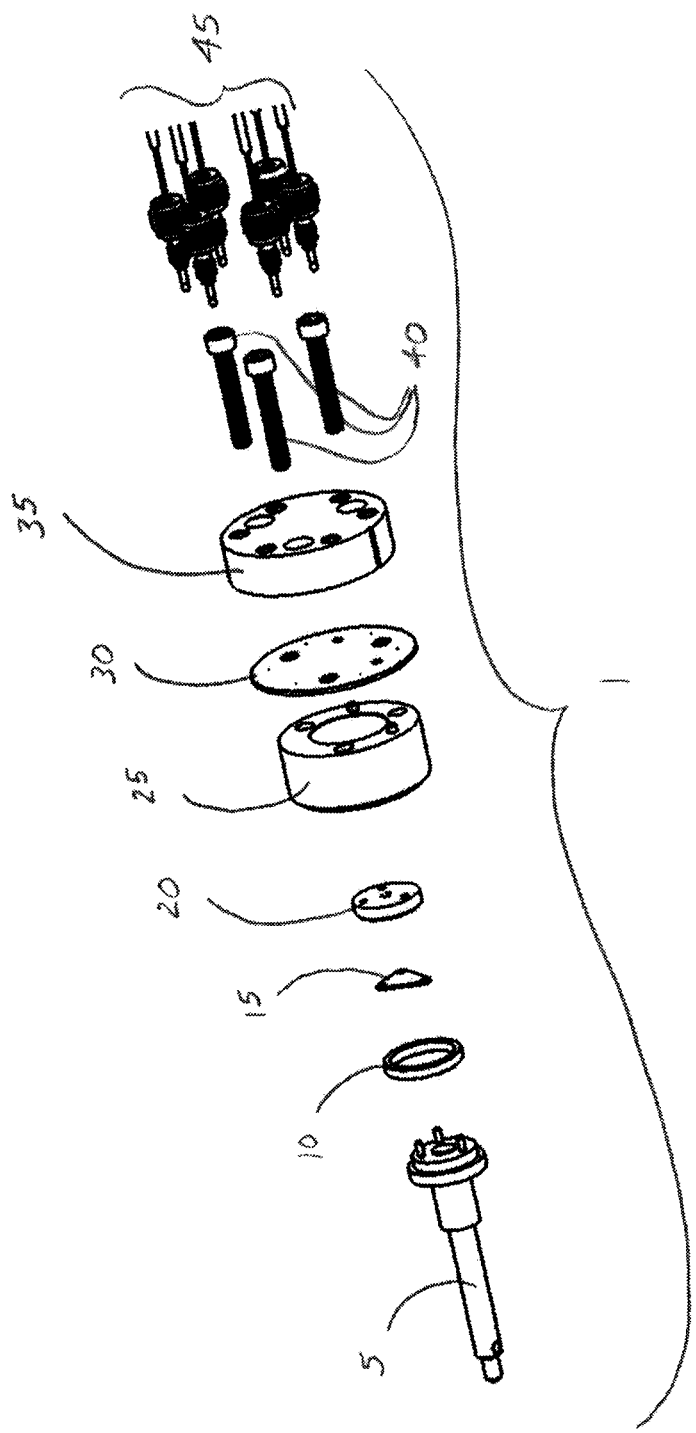
FIG. 1 is an exploded isometric view of certain of the components of a valve in one embodiment in accordance with the present disclosure.
Figure 2:
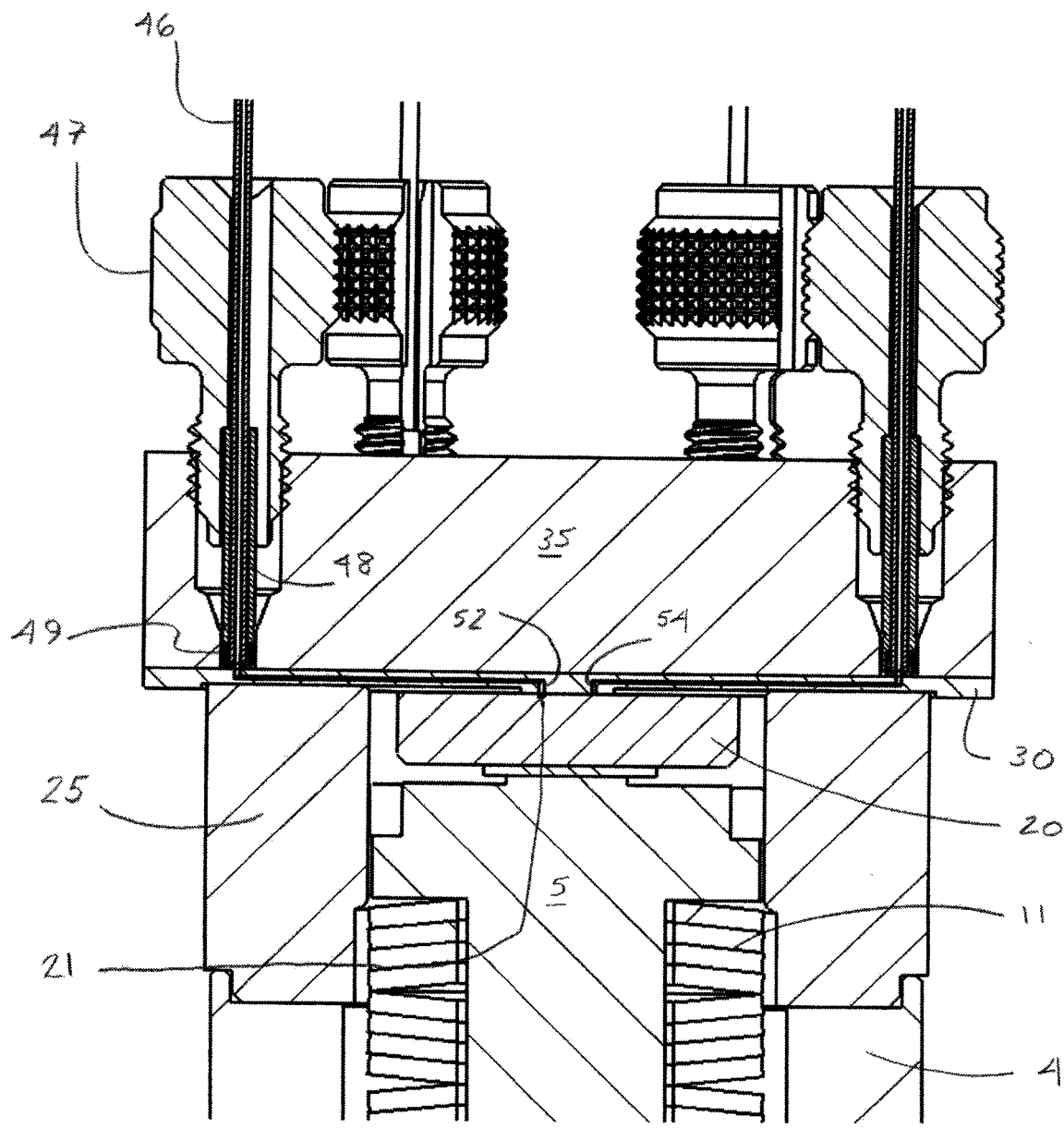
FIG. 2 is a partial cross-sectional view of a valve in one embodiment in accordance with the present disclosure.

Referring to FIG. 1, the key components of a valve 1 in one particular embodiment are shown in an exploded view. The valve 1 includes a rotor shaft 5, a bearing ring 10, a compliant PEEK spring 15, a rotor seal 20, a stator ring 25, a stator face 30, a mounting device 35, a plurality of screws 40, and fitting assemblies with tubing therein 45. A cross-sectional view of a portion of the valve 1 is provided in FIG. 2, with the various components assembled. As shown in FIG. 2, the valve 1 includes a rotor shaft 5, rotor seal 20, stator face 30, and mounting device 35, as well as a housing 4 and, located within the housing 4 and around a portion of rotor shaft 5 is a spring 11. (Screws 40 are not shown in FIG. 2, but it will be appreciated by those skilled in the art that the screws 40 are used to attach the mounting device 35 and stator face 30 to the stator ring 25, which attachment may be either removable or permanent.)

As shown in FIGS. 1 and 2, each of the rotor shaft 5, bearing ring 10, spring 15, rotor seal 20, stator ring 25, stator face 30, and mounting device 35 are generally circular in a transverse direction and, with the exceptions described below (such as in the stator face 30 and in the use of three screws 40), each of such components is generally symmetric around the longitudinal axis of the valve 1 and generally define a cylindrical shape. As shown in FIG. 2, the rotor seal 20, the rotor shaft 5, and the spring 11 are located within the body of the valve 1 as provided by the stator ring 25 and the housing 4. Although the valve 1 shown and described herein is a rotary valve, those skilled in the art will appreciate that the embodiments of the present disclosure may include other valves as well. For purposes of brevity, the present disclosure focuses on a rotary valve.

As shown in FIG. 2, each of the mounting device 35, stator face 30, rotor seal 20, and stator ring 25 have two surfaces, each of which is substantially planar in a transverse direction. For convenience of the reader, these may be referred to as the "top" and "bottom" surfaces with references to the figures. However, those skilled in the art will understand that in fact the valve 1 may have any orientation in use and that the top and bottom of the various components as shown in FIG. 2, for example, may be reversed or may vary in any given use, and that all such orientations are within the scope of the present disclosure. As shown in FIG. 2, the top surface of the stator ring 25 is in contact with portions of the bottom surface of the stator face 30. In addition, a portion of the top surface of the rotor seal 20 is in contact with a central portion of the bottom surface of the stator face 30. The top surface of the stator face 30 is in contact with the bottom surface of the mounting device 35.

The mounting device 35 includes openings or ports for removably receiving tubing 46 and fitting assemblies 45, each of which may include a nut 47, a sleeve 48 and a sealing tip 49. Such fitting assemblies are described in more detail in co-pending U.S. patent application Ser. No. 14/922,041, which was published as U.S. Published Patent Application No. 2016/0116088 A1, and the entirety of which is hereby incorporated by reference as if fully set forth herein. For purposes of brevity, details regarding the nut 47, sleeve 48, and sealing tip 49 are not provided herein, as a full and detailed description is available to the reader in U.S. Published Patent Application No. 2016/0116088 A1.

It will be appreciated that the use of a fitting assembly like that shown and described in detail in U.S. Published Patent Application No. 2016/0116088 A1 in connection with the novel mounting device 35 and stator plate 30 as shown and described herein provides a number of substantial advantages. For example, the use of such fitting assemblies with the mounting device 35 and stator plate 30 allow the tubing to be sealingly engaged with the mounting plate 35 and the stator plate 30 in an essentially vertical position with respect to the longitudinal axis of the tubing and the substantially planar bottom surface of the mounting plate 35 and substantially planar top surface of the stator plate 30. In the past, conventional stators for high pressure valves typically had fluid pathways and ports which were at angles of between 15 and 60 degrees with respect to the substantially planar bottom surface of the stator, such as can be seen in U.S. Pat. No. 5,419,208, for example. By allowing for an essentially vertical or perpendicular connection of the tubing (e.g., between about 80 degrees to 100 degrees with respect to the transverse axis of the stator plate), the mounting device 35 and stator plate 30 allow for sealing the end of the tubing adjacent to or very close to the top surface of the stator plate 30. In addition, this approach means that the costly, and time-consuming machining required to manufacture conventional stators is not required for the mounting plate 35 of the present disclosure. Such machining was costly due to the precision needed to make such ports and fluid pathways in conventional stators. However, the precision required for the mounting device 35 of the present disclosure is much less and much easier to achieve without the costly and time-consuming machining required for conventional stators. Those skilled in the art will understand, however, that any one of a variety of different fitting assemblies may be used to removably and sealingly attach tubing 46 to the valve 1 via the ports in the mounting device 35, and that flat-bottomed fitting assemblies (such as may be commercially available from a variety of manufacturers, including but not limited to the MarvelX fitting assembly from IDEX Health & Science LLC) will likely provide advantages over fitting assemblies with a conical ferrule and cone-shaped port configuration (although the latter may be used with the mounting device 35 and stator plate 30 if desired).

Also shown in FIG. 2 are fluid passageways 52 and 54 located in stator face 30. Each of passageways 52 and 54 provide a fluid pathway between one of the openings (e.g., a bottom of a port) in the mounting device 35, through a corresponding opening in the top surface of the stator face 30, and to a central opening on the bottom of the stator face 30. The rotor seal 20 in FIG. 2 includes a channel 21, which provides a fluid pathway to connect the opening on the bottom face of stator plate 30 corresponding to pathway 52 with at least one other opening in the bottom face of stator plate 30. It will be appreciated that the components of the valve 1 are expected to be attached or in contact with one another so that they form a sealing engagement, even when the fluid flowing through tubing 46 and passageways 52 and 54 is flowing at very high pressures. Spring 11 provides a compressive force against the rotor shaft 5 and urges the top side of rotor shaft 5 against the bottom side of the rotor seal 20, and thus the top side of rotor seal 20 against the bottom side of the stator face 30.

The passageways 52 and 54, as well as the channels 21 may be of various shapes and sizes. For example, the passageways 52 and 54 and/or channels 21 may be circular in cross section, a hemisphere in cross section, D-shaped in cross section, square shaped in cross section, and so forth. Passageways 52 and 54 and/or channels 21 can also have different sizes or shapes from one another if desire, such that passageway 52 has a first shape and/or size and passageway 54 has a second shape and/or size, for example. Although FIG. 2 shows passageways 52 and 54 located within stator face 30, it will be appreciated that fluid pathways can be provided as a groove on the bottom face of the stator face 30, as the top side of rotor seal 20 will close or seal such grooves when the valve 1 is fully assembled. Alternatively, fluid pathways can be provided as one or more grooves or channels 21 on the top side of the rotor seal 20, and in addition a combination of passageways and/or grooves on the top and/or bottom sides of the stator face 30 can be provided. Moreover, those skilled in the art will appreciate that, although FIG. 2 shows two passageways 52 and 54, and one channel 21, more or less passageways (or grooves, as the case may be), and/or channels in rotor seal 20, can be provided in valve 1.

Although not shown, those skilled in the art will appreciate that the stator plate 30 may comprise one or more analytical instrument components, such as a sample loop, a splitter, a mixer, a column, a temperature, fluid flow, or pressure sensor, a filter, a heating element, a detector, and other types of micro-electro mechanical systems components. Techniques for adding such components to a substrate with the use of diffusion bonding that may be useful in manufacturing a stator face 30 having one or more such components are detailed in U.S. Published Patent Application No. 2016/0169843 A1, which was published on Jun. 16, 2016, and is entitled "Pressure Sensing and Flow Control In Diffusion-Bonded Planar Devices for Fluid Chromatography," which is hereby incorporated by reference herein as if fully set forth herein.

Figure 3:
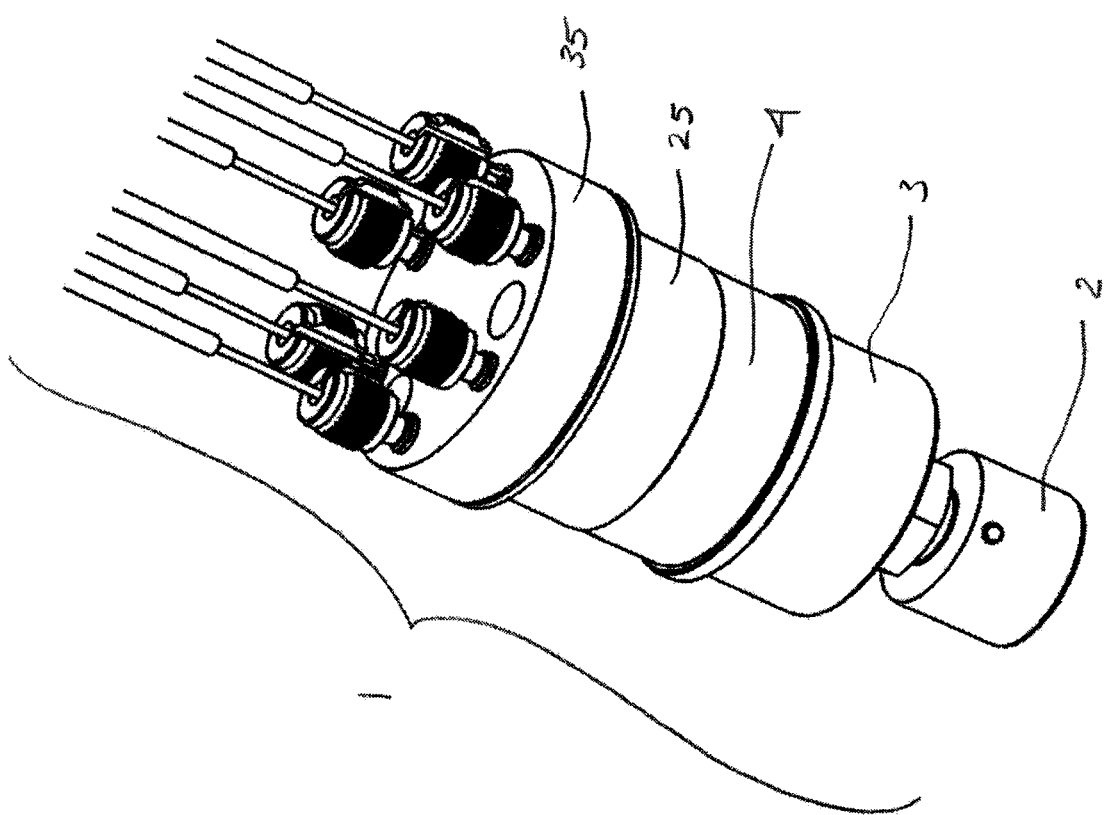
FIG. 3 is an isometric view of a valve in one embodiment in accordance with the present disclosure.

In FIG. 3, an isometric view of an assembled valve 1 is provided. As shown in FIG. 3, the valve 1 includes the mounting device 35, the stator ring 25, and also valve body 3 and a knob 2. The knob 2 can be attached to one end of a rotor shaft 5, and that when the knob 2 is turned, the rotor shaft 5 and rotor seal 20 are also turned or rotated. It will also be appreciated that some or all of the fluid pathways and/or passageways (however shaped or whether grooves or passageways, etc.) may be coated with one or more coatings. Coatings may be added to such fluid pathways to reduce friction, increase hardness, provide biocompatibility (or enhance existing biocompatibility), provide better chemical compatibility, and the like, all as may be desired for one or more particular applications of the valve 1. For example, it may be desirable to have the fluid pathways coated with a particular chemical substance if the intended application involves the use of a corrosive chemical, or to have biocompatible fluid pathways if the intended application involves biological samples and biocompatibility is a concern.

Among other advantages of a valve with the two-piece mounting device 35 and stator face 30 as described herein, the mounting device 35 can be made of plastics or metal because the mounting device 35 does not form a part of the fluid flowpath and does not come into contact with the fluid. For example, the mounting device 35 can be made of plastics, such as PEEK, PPS, DELRIN, PP, PS, ULTEM, and the like, or the mounting device 35 can be made of metal, such as aluminum, copper, steel, stainless steel, titanium, MP35N, or alloys of various metals, or of ceramic materials or other composite materials. As long as the stator plate 30 is made of one or more biocompatible materials, the valve 1 can still provide a biocompatible flowpath and the valve 1 can be used for biocompatible applications. Another advantage of the two-piece assembly is that the mounting device 35 can be made of a cheaper material, such as for those applications in which higher pressures are not used, and it can be reusable. Thus, the valve 1 of the present disclosure provides a great deal of flexibility in terms of materials and potential uses, as well as cost savings and ease of manufacturing.

Although not shown, it will be appreciated that either or both of the substantially planar surfaces of the stator face 30 may be lapped and/or coated with a diamond-like carbon (DLC) or other coating material, and the substantially planar surface of the mounting device 35 which abuts one surface of the stator plate 30 may also be lapped and/or coated with DLC or another coating material. Such lapping and/or coating can be used to reduce friction and increase hardness and to provide a very smooth surface to provide a better fit and engagement of the mounting device 35 and one side of stator face 30 and the rotor seal 20 and the second side of the stator face 30, respectively.

Another advantage of the valve 1 with the two-piece stator assembly with the mounting device 35 and the stator plate 30 is that the stator plate 30 can be removed and replaced with a different stator face 30. For example, if a first stator plate 30 has been used extensively and starts to become worn or provides less precise results, the first stator plate 30 can be replaced without requiring a new valve or even a new mounting device 35. For example, an operator can disassemble the valve 1 with a worn stator plate 30 by unscrewing the three screws 40 and removing the stator face 30 and the mounting device 35 from the stator ring 25 of the valve 1. The worn stator face 30 can then be detached from the mounting device 35 and a new stator face 30 can be attached to replace the worn stator face 30, and then the operator can reassemble the valve 1 by aligning the stator face 30 and the mounting device 35 with location pins (not shown) and then securely attaching the stator face 30 and the mounting device 35 to the stator ring 25 and valve 1 by screwing the screws 40 into place in the body of the valve 1 to securely attach the mounting device 35 and new stator face 30 to the rest of the valve 1. This provides the advantage of replacing the stator face 30 without replacing any other components of valve 1, thereby providing longer life and cheaper costs of use of the valve 1.

Moreover, the stator face 30 and/or mounting device 35 can be replaced with these methods so that an alternative stator face 30 and/or alternative mounting device 35 can be used for a desired application. Because analytical instrument systems can be complicated, allowing an operator to simply replace a stator face 30 and/or mounting device 35 for a given application of the valve allows the operator to use essentially the same valve 1 for a variety of applications. For example, an operator may wish to use a metallic mounting device 35 and a metallic stator face 30 in combination for a particular application, such as one involving high pressures. If the operator then desires to use the valve 1 in an application in which biocompatibility is desired, the operator can then replace either or both of the stator face 30 and the mounting device 35 with a stator face and/or mounting device which are made from biocompatible materials. In addition, an operator can replace a stator face 30 for an application in which it is desired that the stator face have a particular size of sample loop, a mixer, a pressure, flow, or temperature sensor, or the like so that the replacement stator face 30 includes the desired feature for the desired application, all without requiring a completely separate valve 1. Such flexibility will provide the operator with the advantages of reduced costs (due to less need for additional valves or replacement valves), longer valve life, ease of use across a variety of applications, and the ability to provide changes to the valve relatively quickly (such as by changing the stator face and/or mounting plate in a valve without entirely replacing or relocating the valve within the analytical instrument system).

Figure 4:
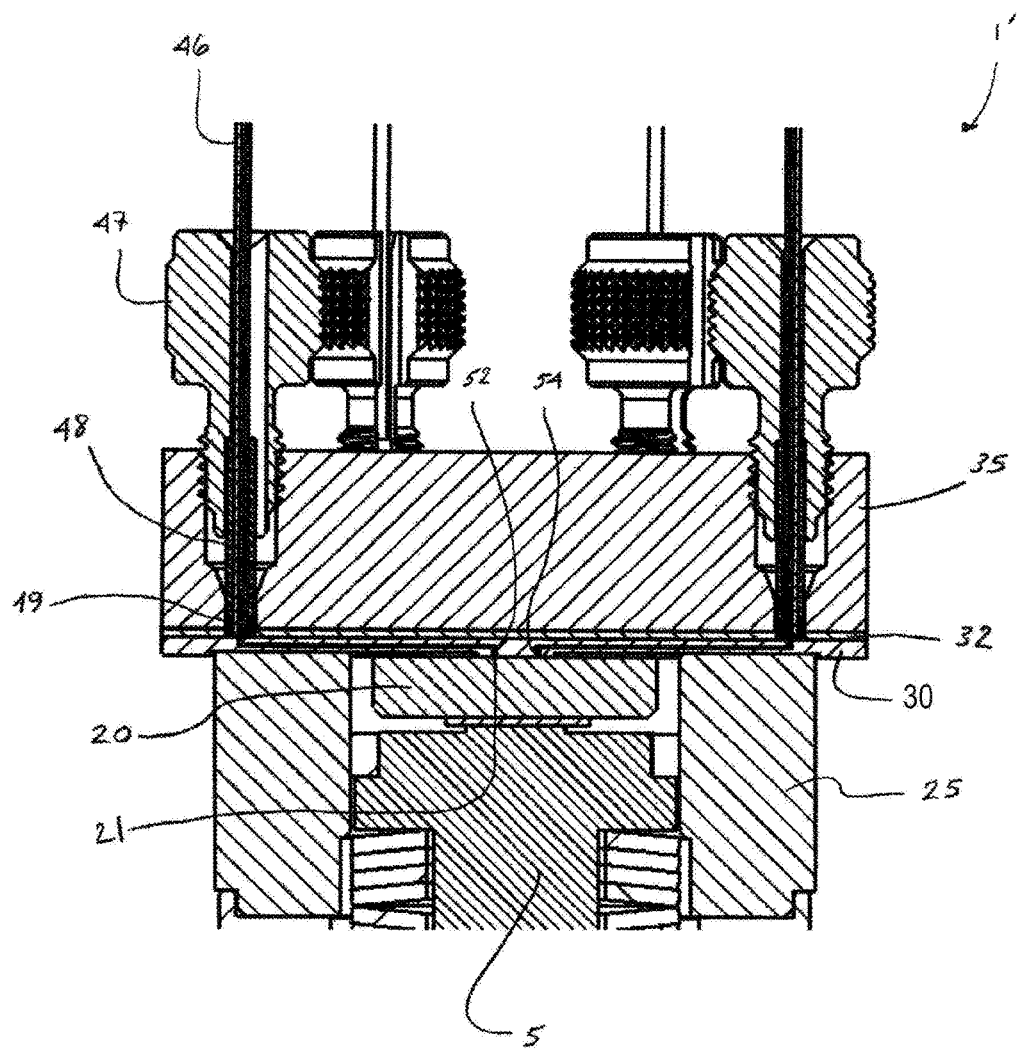
FIG. 4 is a partial cross-sectional view of a valve in another embodiment in accordance with the present disclosure.

Referring now to FIG. 4, an alternative embodiment of valve 1' is shown. (It will be appreciated that for the convenience of the reader, like components and features in various drawings will have the same numbers.) The valve 1' includes a mounting device 35 and is shown with four tubes 46 connected to four ports therein. The valve 1' further has a rotor shaft 5 and a rotor seal 20. Instead of the stator face 30 shown in FIGS. 1-3, the valve 1' in FIG. 4 has a guide layer 32 and a bottom stator face 31. The guide layer 32 provides a guide surface to help guide the tip of the tubing 46 into the guide layer 32 and into contact with the top surface of the bottom stator face 31.

Figure 5:
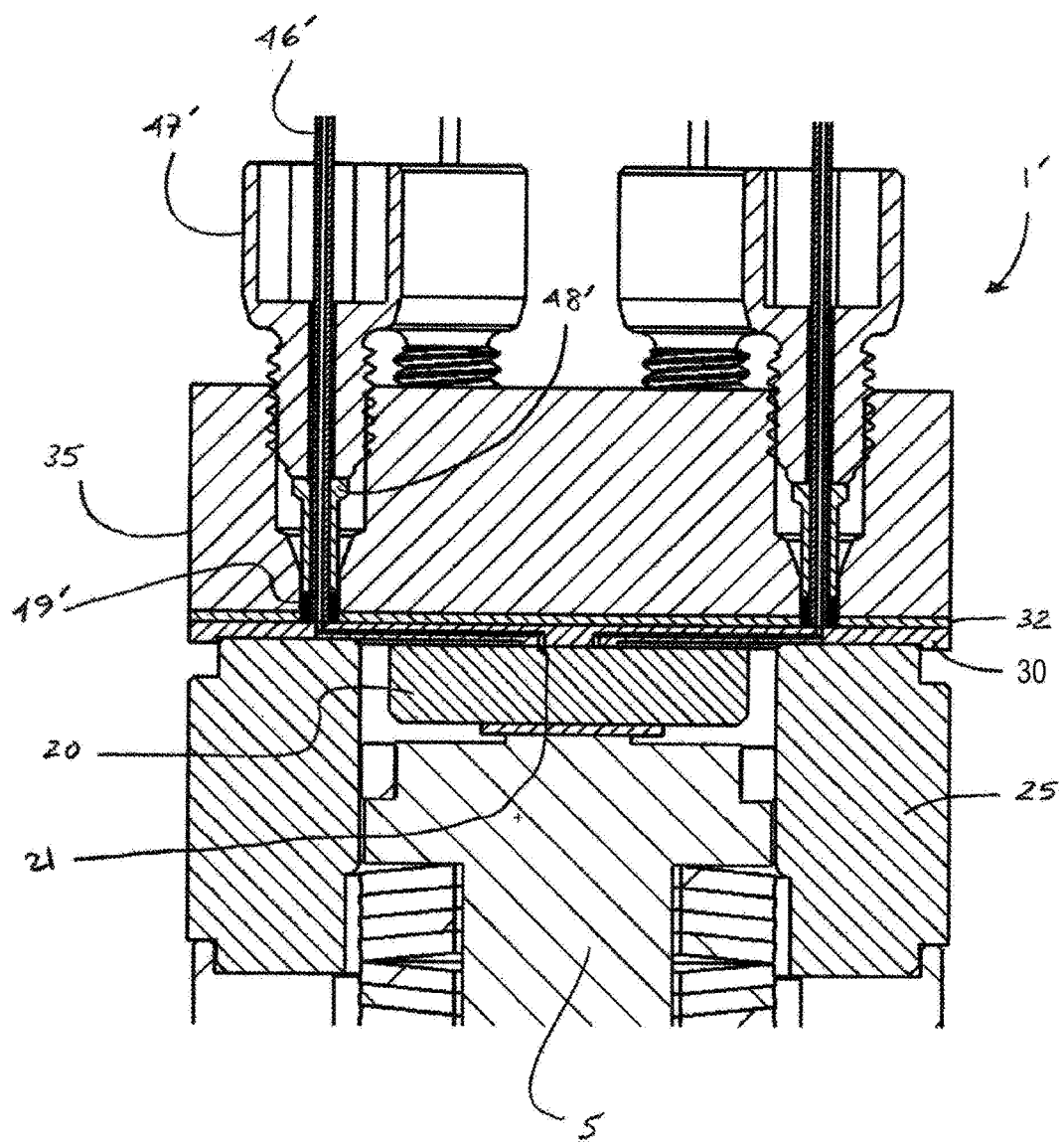
FIG. 5 is a partial cross-sectional view of a valve in another embodiment in accordance with the present disclosure.

In FIG. 5, the valve 1' is shown. However, in FIG. 5, the tubing 46', nut 47', sealing tip 49' and sleeve 48' are provided. Thus, FIG. 5 illustrates an alternative embodiment in which an alternative fitting assembly may be used, even though no change to the mounting device 35, guide layer 32 or bottom stator face 31 (or other components) of valve 1' is required. A commercially available fitting assembly like that shown in FIG. 5 can be provided by the VIPER brand fitting assembly from Dionex Corporation of Sunnyvale, Calif.

Figure 6:
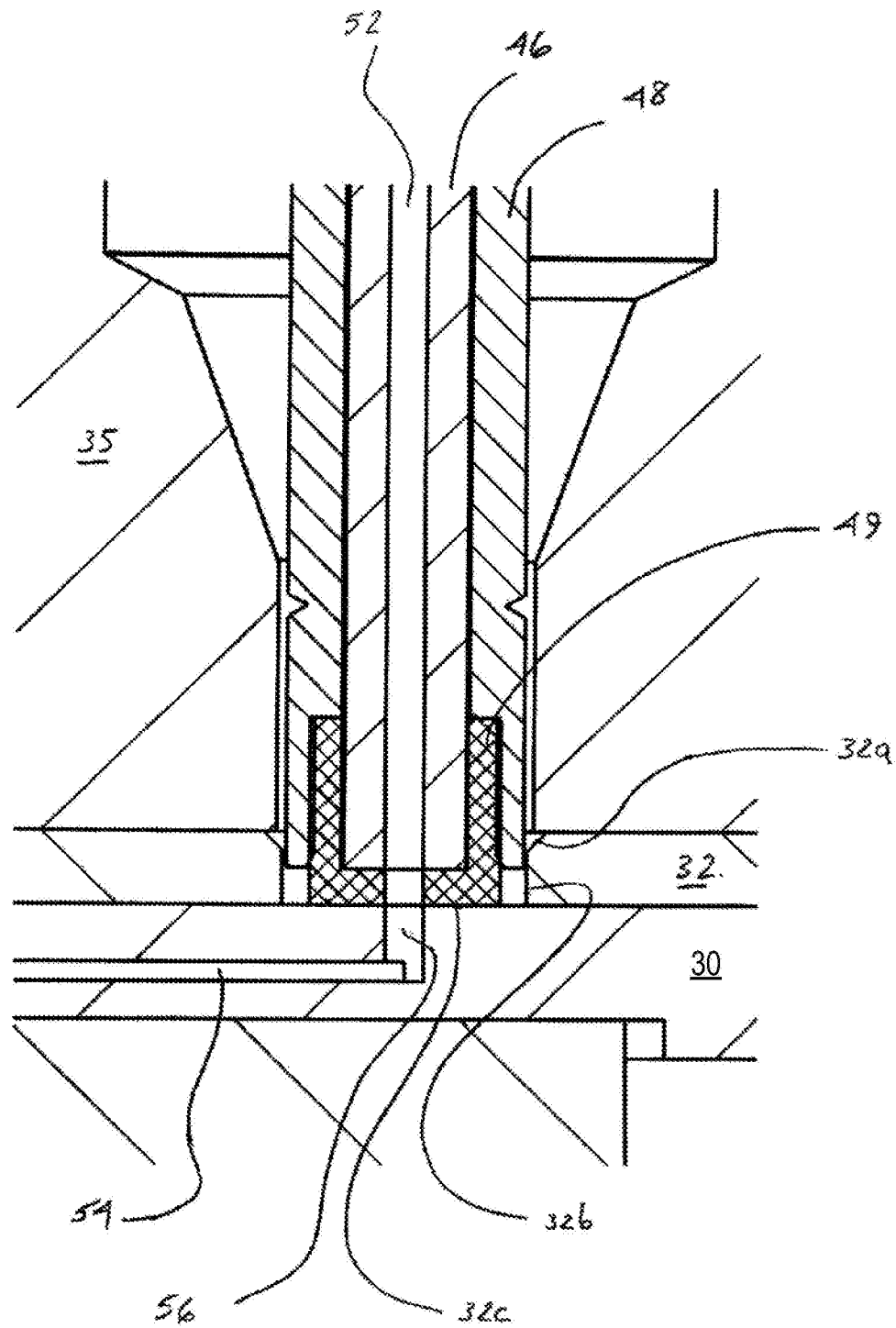
FIG. 6 is an enlarged partial cross-sectional view of a valve in another embodiment in accordance with the present disclosure.

FIG. 6 provides an enlarged partial cross-sectional view of the interface between the mounting device 35, the guide layer 32, and the bottom stator face 31. As shown in FIG. 6, tubing 46 with a central fluid passageway 52 is shown located within a passageway through sleeve 48. At the bottom end of the tube 46, a sealing tip 49 is provided, with a bottom portion of the sleeve 48 surrounding the bottom outer surface portion of the sealing tip 49. As also shown in FIG. 6, the bottom end surface of the sealing tip 49 is in contact with the top surface of the guide layer 32. The guide layer 32 has an opening 32b therein which is adapted to snugly receive therein at least a portion of the bottom of the tube 46, sleeve 48, and sealing tip 49. In addition, the opening 32b in the guide layer 32 has a portion 32a which has a wider inner diameter than the bottom portion of the opening 32b. This wider portion 32a (which is generally frustoconical in shape) helps align the combination of the sealing tip 49, sleeve 48, and tube 46 so that the passageway 52 of the tube 46 is in good alignment with the opening 32b in the bottom stator face 31.

Figure 7:
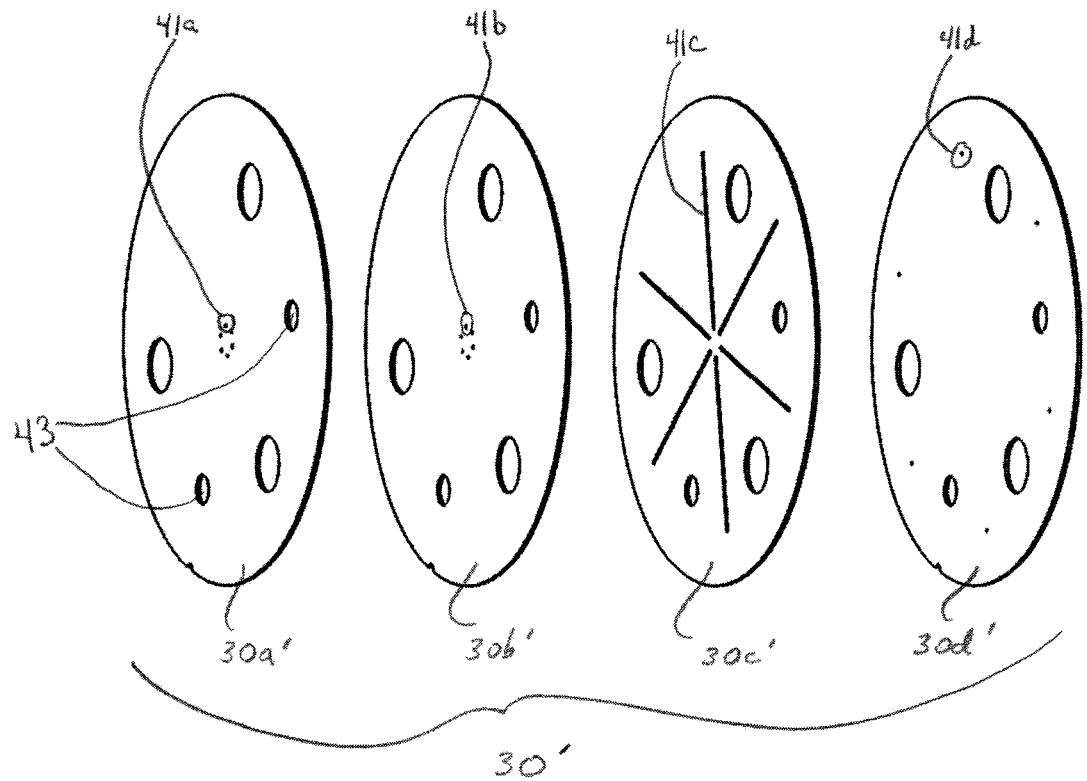
FIG. 7 is an exploded isometric view of the portions of a stator plate in another embodiment in accordance with the present disclosure.

Turning now to FIG. 7, an exploded isometric view of a series of layers 30a', 30b', 30c' and 30d' are shown, which together can form stator face 30'. In FIG. 7, it can be seen that layer 30a' has an opening 41a, which is one of six openings which are located in a circular pattern proximal the center of the layer 30a'. Also shown in FIG. 7 with respect to layer 30a' are two openings 43, through which location pins (not shown) are located when the valve is assembled. It can be seen that each of layers 30b', 30c', and 30d' has openings which correspond to and align with the openings 43 of the layer 30a'. In addition, (and among the other openings and fluid pathways shown in FIG. 7) layer 30b' has an opening 41b, layer 41c has a pathway 41c, and layer 30d' has an opening 41d. It will be appreciated from FIG. 7 that openings 41a, 41b, the ends of pathway 41c, and opening 41d, respectively, are aligned and correspond to one another, thus providing a fluid pathway therebetween. Those skilled in the art will understand that, although not described in detail for purposes of brevity, the other openings and channels shown in FIG. 7 are aligned and correspond to respective openings and at least one channel in layers 30a', 30b', 30c', and 30d'.

Figure 8:
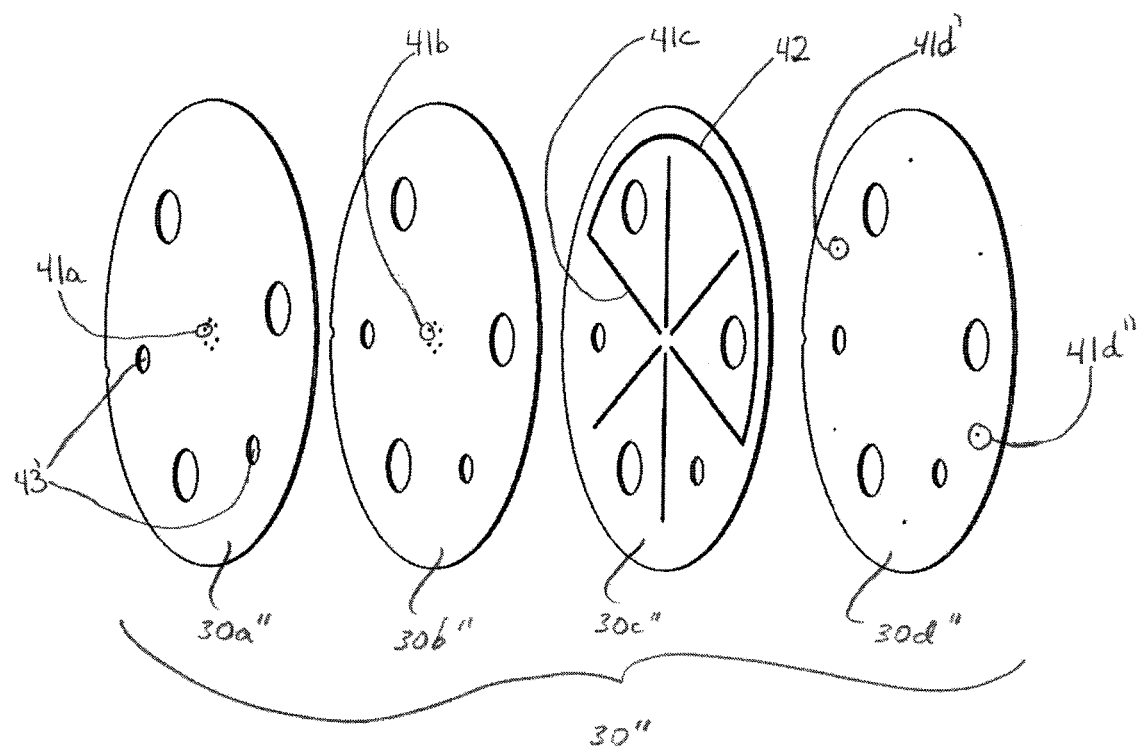
FIG. 8 is an exploded isometric view of the portions of a stator plate in another embodiment in accordance with the present disclosure.

In FIG. 8, an alternative stator face 30" is shown in an exploded isometric view. The stator face 30" includes layers 30a", 30b", 30c", and 30d". In this particular embodiment, the main difference between it and the embodiment of stator face 30' shown in FIG. 7 is that the stator face 30" includes a layer 30c" in which grooves or fluid pathways are shown in a different configuration from that shown in FIG. 7. In FIG. 8, it can be seen that layer 30a" has an opening 41a', which is one of six openings which are located in a circular pattern proximal the center of the layer 30a". Also shown in FIG. 8 with respect to layer 30a" are two openings 43, through which location pins (not shown) are located when the valve is assembled. It can be seen that each of layers 30b", 30c", and 30d" has openings which correspond to and align with the openings 43 of the layer 30a". In addition, (and among the other openings and fluid pathways shown in FIG. 8) layer 30b" has an opening 41b', layer 41c" has a pathway 41c', and layer 30d" has an opening 41d'. In addition, layer 30c" has a sample loop 42 provided by a channel connecting channel 41c' with a corresponding channel opposite thereto. It will be appreciated from FIG. 8 that openings 41a', 41b', the ends of pathway 41c' and sample loop 42, and openings 41d' and 41d", respectively, are aligned and correspond to one another, thus providing a fluid pathway therebetween. Those skilled in the art will understand that, although not described in detail for purposes of brevity, the other openings and channels shown in FIG. 8 are aligned and correspond to respective openings and at least one channel in layers 30a", 30b", 30c", and 30d".

Figure 9:
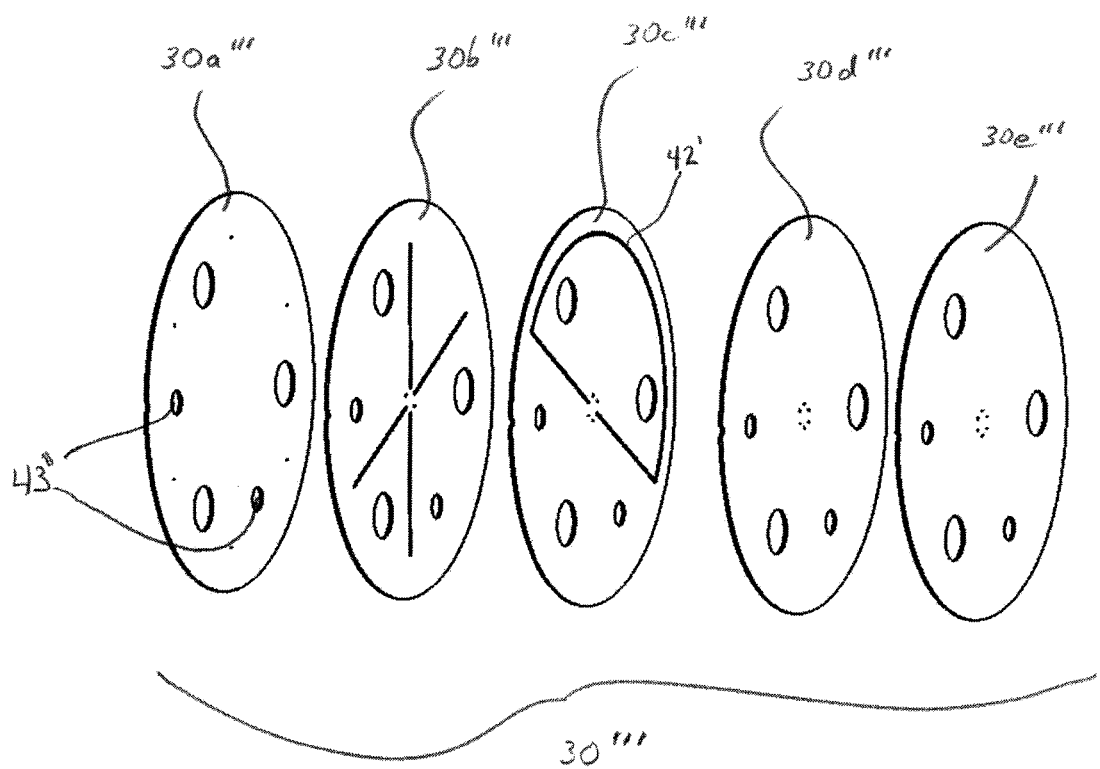
FIG. 9 is an exploded isometric view of the portions of a stator plate in another embodiment in accordance with the present disclosure.

FIG. 9 provides yet another alternative embodiment of a stator face 30'" in an exploded isometric view. In FIG. 9, a stator face 30'" is shown, which includes five pieces or slices 30a'", 30b'", 30c'", 30d'", and 30e'". As shown in FIG. 9, the pieces 30b'" and 30c'" provide different fluid pathway configurations than those shown and provided by the stator face 30' or the stator face 30" shown in FIGS. 7 and 8, respectively, including among other things a sample loop 42' in layer 30c'". Those skilled in the art will appreciate that features such as but not limited to sample loops may have different sizes, lengths, patters, and volumes, among other things, as may be desired for a given application, and that there are many other configurations of the fluid pathways and fluid connections that can be provided with a stator face 30 beyond the various particular embodiments shown in FIGS. 7-9, for example.

Figure 10:
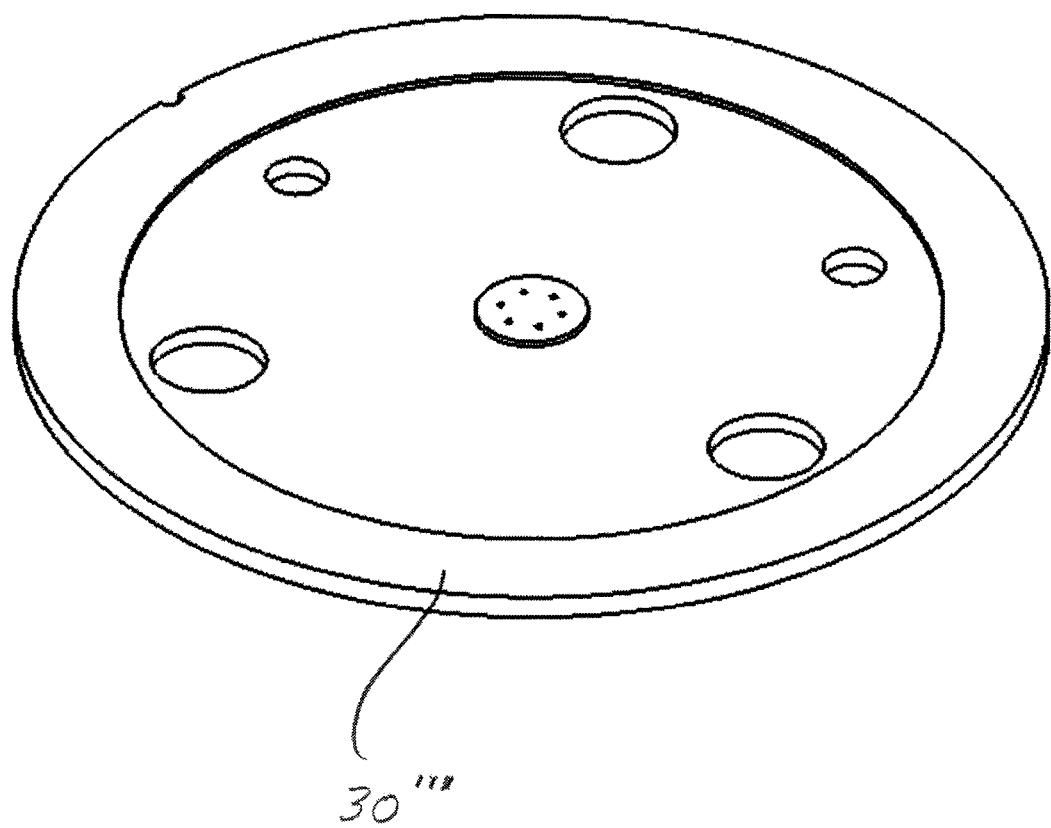
FIG. 10 is an isometric view of a stator plate in an embodiment in accordance with the present disclosure.

The different layers 30a'", 30b'", 30c'", 30d'", and 30e'", for example, can be attached and combined into a single stator face 30'" (such as shown in FIG. 10) by diffusion bonding. The plurality of holes in each of the layers and also the grooves or fluid pathways in each of the layers 30b'" and 30c'", for example, can be etched into the layers so that the holes and grooves or pathways are very precisely located and of very precise sizes and shapes. The stator face 30'" shown in FIG. 10 further includes an annular ring shape with a thicker width than the interior portion of the stator face 30'". Such an annular ring shape can be obtained by machining or etching the combination of the layers 30a'", 30b'", 30c'", 30d'", and 30e'" into the stator face 30'".

If layers 30a'", 30b'", 30c'", 30d'", and 30e'" are made of a metal, such as titanium or any of the metals or alloys noted above, such layers 30a'"-30e'" can be bonded together by diffusion bonding. Diffusion bonding techniques that may be appropriate for bonding layers 30a'"-30e'" together are described in U.S. Published Patent Application No. 2010/0171055 A1, published on Jul. 8, 2010, and entitled "Liquid-Chromatography Apparatus Having Diffusion-Bonded Titanium Components," which is hereby incorporated by reference herein as if fully set forth herein. Among other things, U.S. Published Patent Application No. 2010/0171055 A1 describes a stator assembly for a valve having layers diffusion bonded together and having a mounting assembly with ports therein diffusion bonded to a combination of several layers which are themselves diffusion bonded together.

Layers 30a'"-30e'" need not be made of metal, however, and may instead comprise ceramic materials, and in particular may comprise layers which may in turn comprise or consist of the same or different ceramic materials with some or all of the layers diffusion bonded together or attached using other means. One approach for making stator face 30'" would be to machine two of the layers, each made of sintered ceramic materials, and then bond these two layers together with a green sheet ceramic layer. After relatively low temperature sintering, the sandwiched green sheet layer bonds the two other layers together. Alternatively, high temperature co-fired ceramic layers may be used to provide the stator face. More detail about techniques for bonding or attaching ceramic layers to one another which may be used for ceramic layers 30a'"-30e'" include those described in U.S. Published Patent Application No. 2009/0321356 A1, which was published on Dec. 31, 2009, and is entitled "Ceramic-Based Chromatography Apparatus and Methods for Making Same," which is hereby incorporated by reference as if fully set forth herein. U.S. Published Patent Application No. 2009/0321356 A1 describes methods and techniques for using ceramic-based tape, referred to as "green sheet" or "green-sheet tape," and further describe the use of ceramic materials such as glass, zirconia, and alumina. Those skilled in the art will appreciate that some or all of layers 30a'"-30e'" can be made of such materials and can be manufactured with the methods and use of green sheet as described in more detail in U.S. Patent Application No. 2009/0321356 A1. It will also be appreciated that the foregoing discussion with respect to layers 30a'"-30e'" applies equally to layers 30a'-30d' for stator face 30', and to layers 30a"-30d" for stator face 30".

Figure 11:
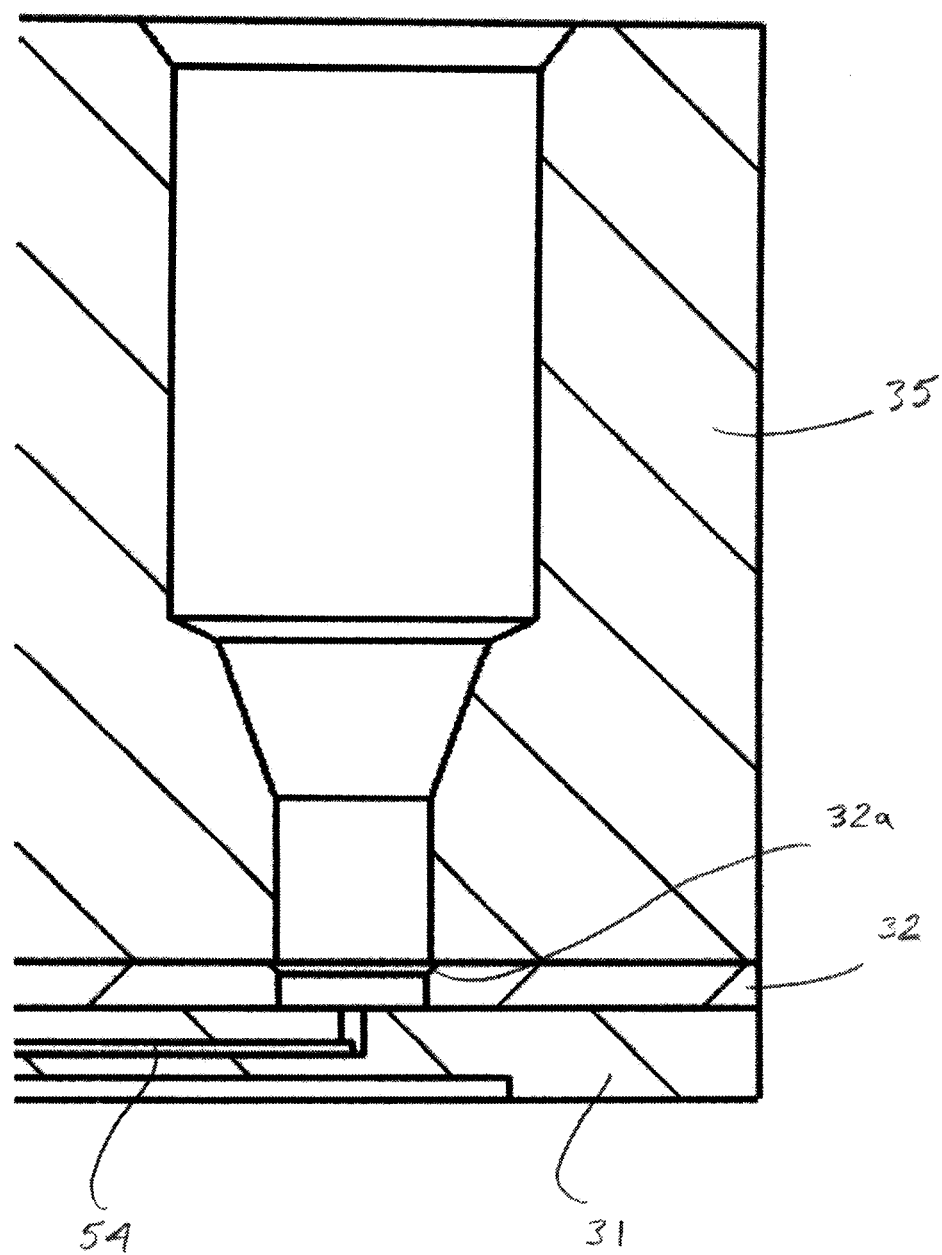
FIG. 11 is an enlarged cross-sectional view of a stator plate and mounting device in an embodiment in accordance with the present disclosure.

FIG. 11 provides an enlarged partial cross-sectional view of an alternative embodiment of a mounting device 35 with a guide layer 32 and a bottom stator face 31. In this particular embodiment, the port of the mounting device 35 has a different configuration. Instead of a port designed for a flat-bottomed fitting assembly (such as is shown in FIG. 6, for example), the port of the mounting device 35 shown in FIG. 11 is configured with a conical portion so that the port is adapted to sealingly and removably receive and hold a fitting assembly with a generally conically-shaped ferrule, a nut, and tubing through the nut and ferrule (not shown).

Figure 12:
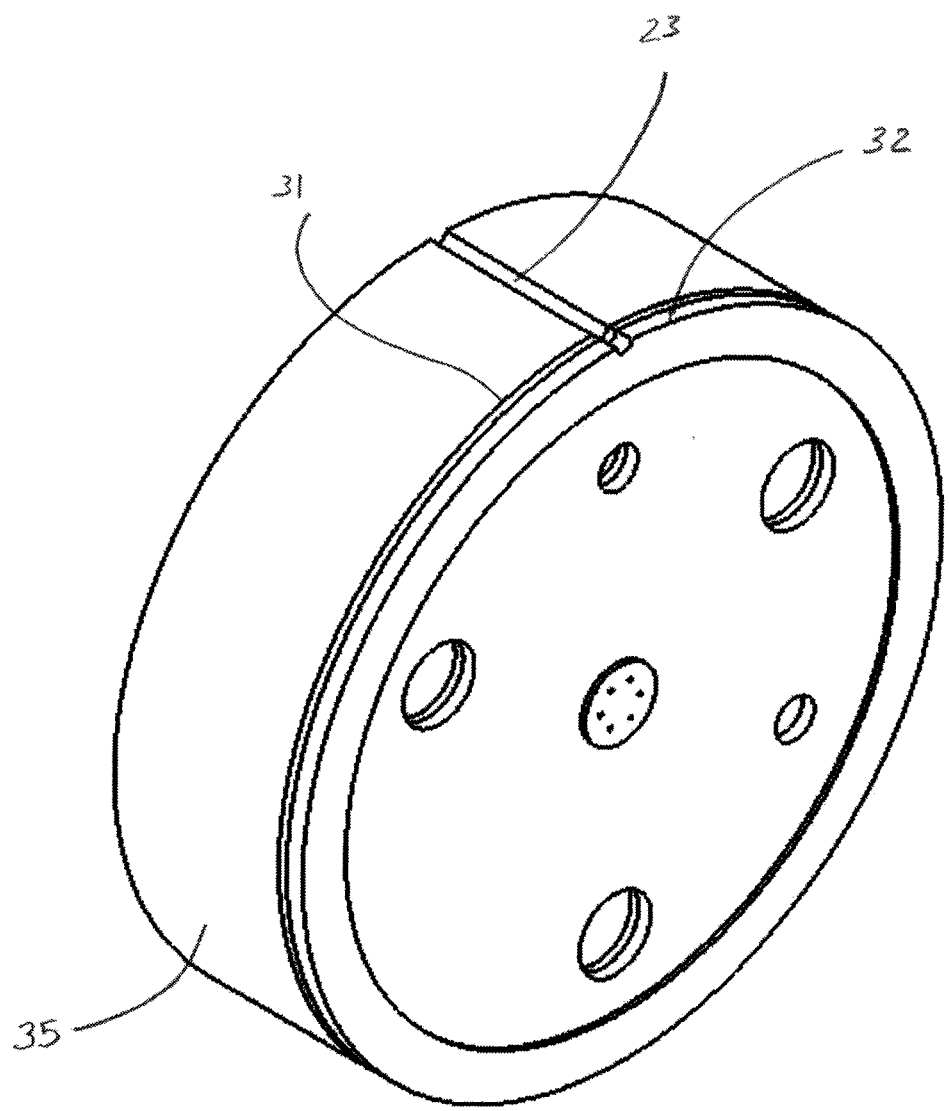
FIG. 12 is an isometric view of a stator plate and mounting device in an embodiment in accordance with the present disclosure.

FIG. 12 provides an isometric view of the stator face 30, which in the embodiment shown in FIG. 12 has a guide layer 32 and a bottom stator face layer 31, as well as the mounting device 35. Shown more clearly in FIG. 12 is a groove 23 which extends longitudinally through each of the guide layer 32, the bottom stator face 31, and the stator ring 25, and along the exterior edge of each. The groove 23 is useful for quick and easy alignment of the different components during manufacture and assembly.

Figure 13:
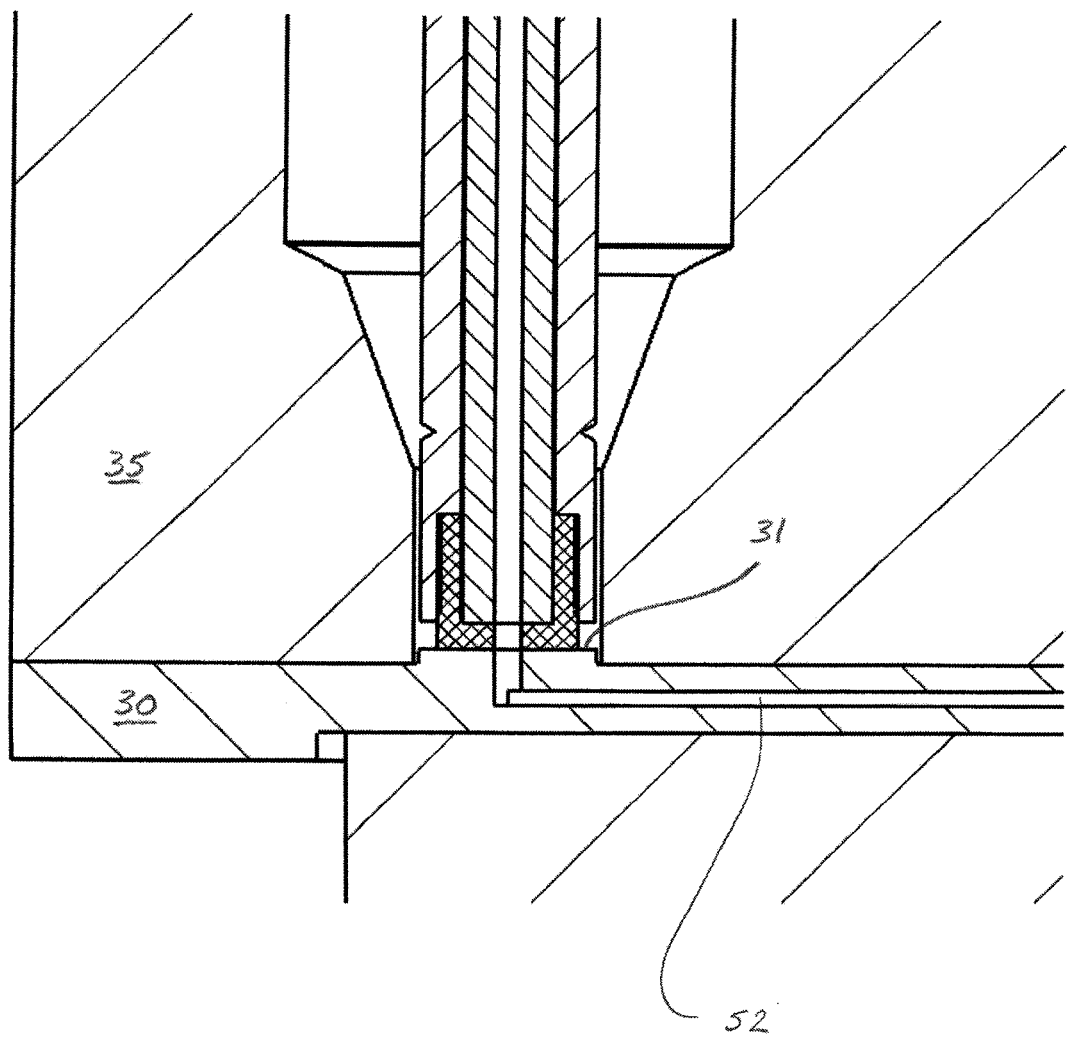
FIG. 13 is an enlarged cross-sectional view of a stator plate and mounting device in another embodiment in accordance with the present disclosure.

FIG. 13 includes an enlarged partial cross-sectional view showing yet another alternative embodiment. In FIG. 13, the stator face 30 includes a boss 31 which is adapted to extend upwardly from the top surface of the stator face 30. In addition, the boss 31 is of a selected shape, size, and location so that, when the stator face 30 and the mounting device 35 are attached to one another, the boss 31 extends upwardly from the top surface of the stator face 30 and provides the bottom surface of the port of the mounting device 35.

Figure 14:
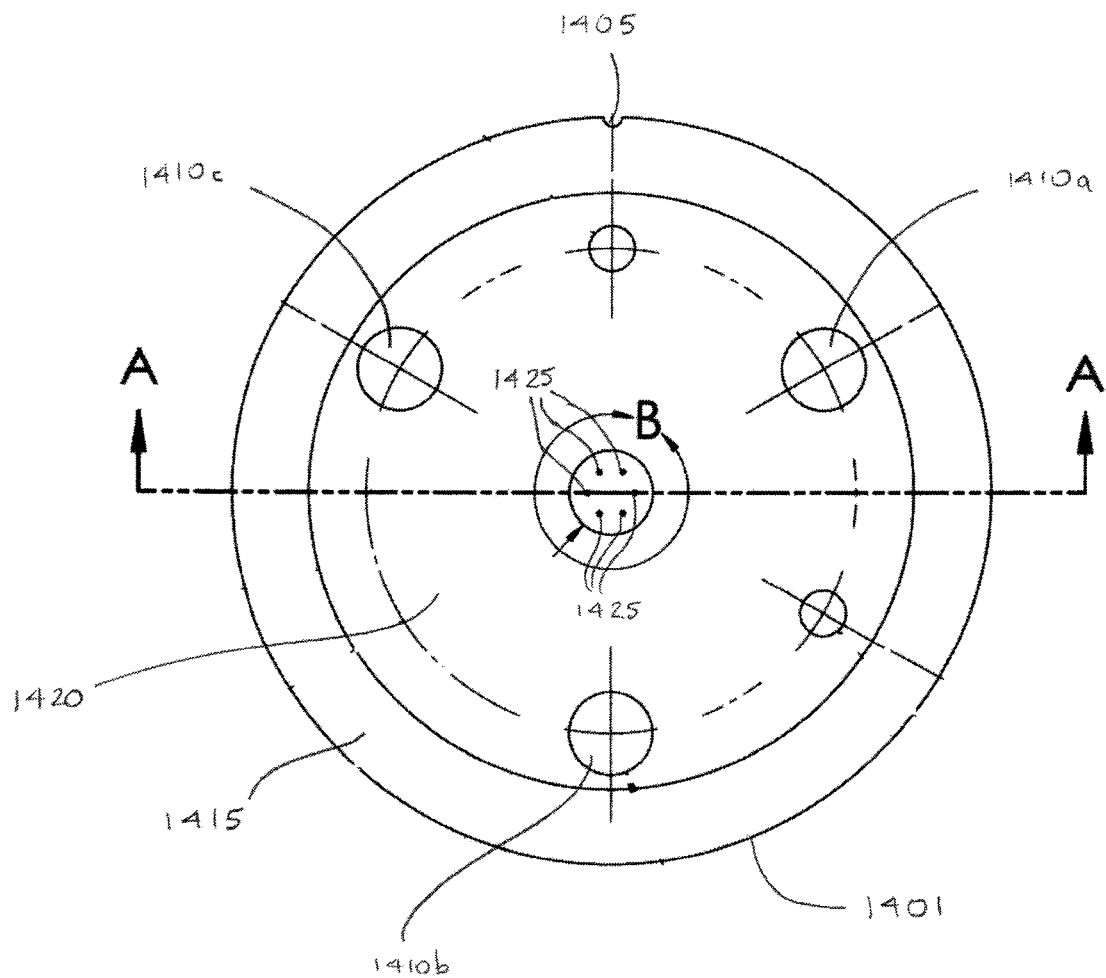
FIG. 14 is a top view of a stator plate in accordance with an embodiment of the present disclosure.

FIG. 14 provides a top view of a stator plate 1401. As shown in FIG. 14, the stator plate 1401 has three holes 1410a, 1410b, and 1410c which are adapted to receive a threaded screw or other means for attached the stator plate 1401 to a mounting device and/or to a housing of a valve body (not shown). It will be appreciated that the stator plate 1401 can be removably attached to the mounting device and/or valve body with threaded screws. In addition, the stator plate 1401 has an outer annular ring 1415, which can have a thicker width than the interior portion 1420 of the stator plate 1401. Located near the center of the stator plate 1401 are six openings 1425, which are adapted to provided fluid pathways and be aligned with openings and/or fluid pathways in a mounting device and/or rotor seal (not shown). Also shown in FIG. 14 is a groove or notch 1405 in the outer edge of the stator plate 1401.

Figure 15:
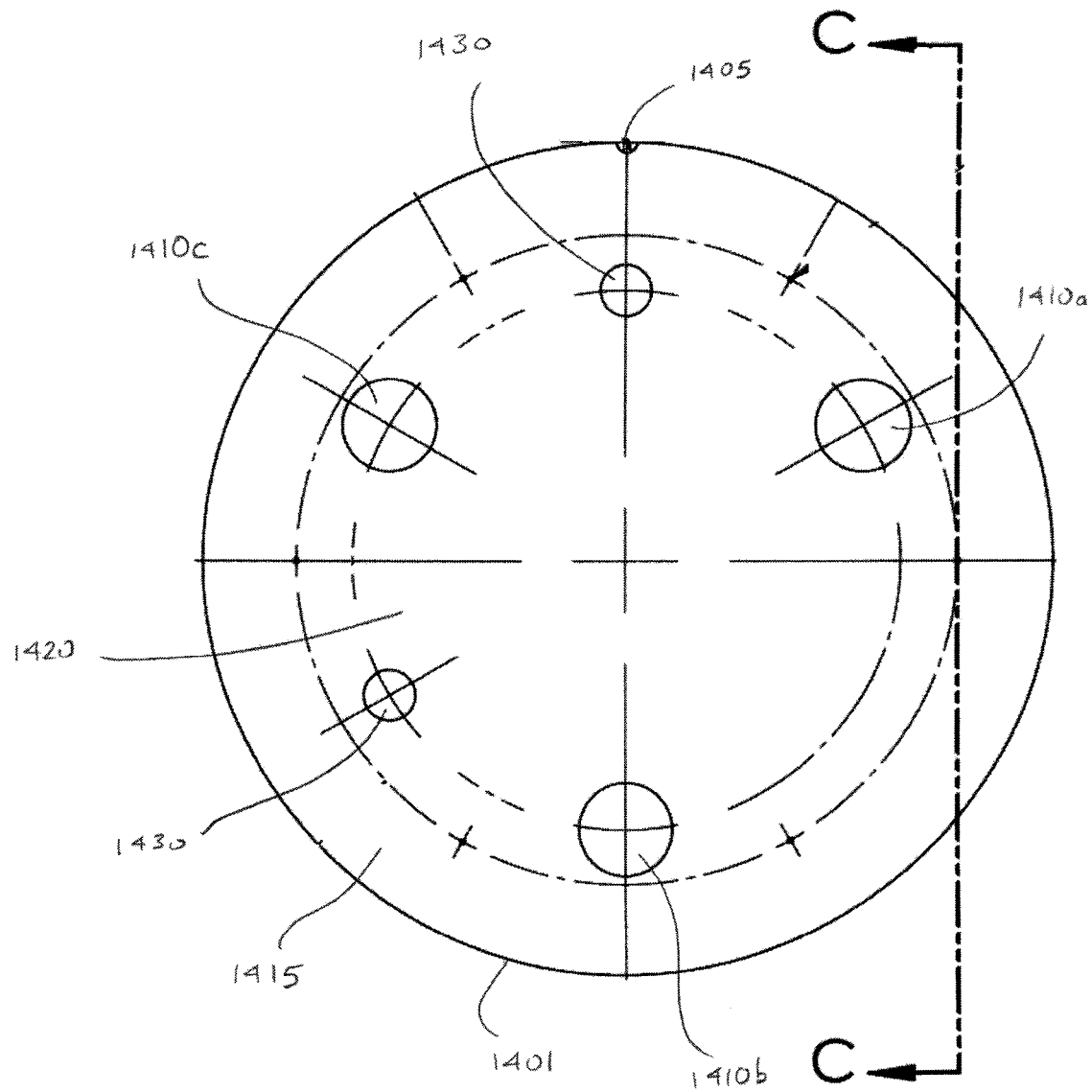
FIG. 15 is a bottom view of a stator plate in accordance with an embodiment of the present disclosure.

FIG. 15 provides a bottom view of the stator plate 1401. Generally, the same features in FIGS. 14-18 have the same numbering for ease of reference. In FIG. 15, openings 1430 can be seen in the bottom side of the stator plate 1401.

Figure 16:
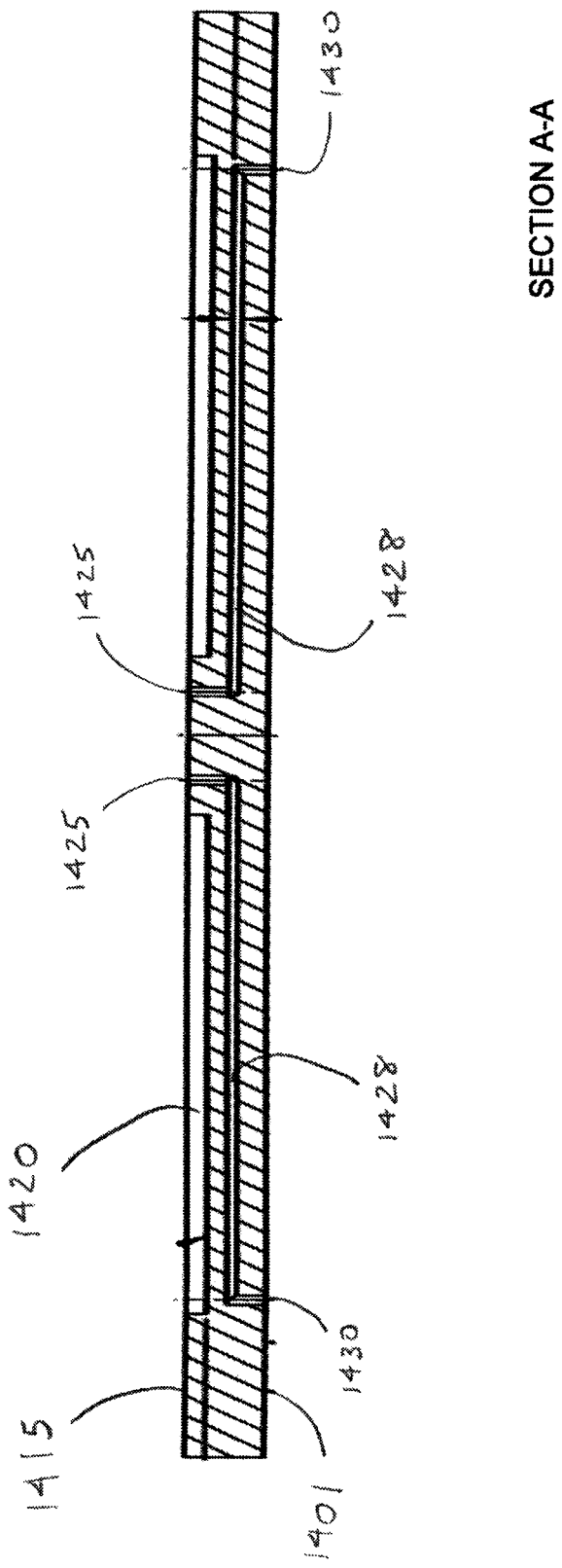
FIG. 16 is a cross-sectional view of a stator plate of FIG. 14 taken along line A-A.

Referring to FIG. 16, a cross-sectional view of the stator plate 1401 taken along line A-A of FIG. 14 is provided. FIG. 16 shows the annular outside ring 1415 of the stator plate 1401, as well as the interior portion 1420, openings 1425 and also openings 1430. As can be seen from FIG. 16, the openings 1425 and 1430 are in fluid communication with one another (i.e., each opening 1425 is in fluid communication with an opening 1430 in this view) via fluid pathways 1428.

Figure 17:
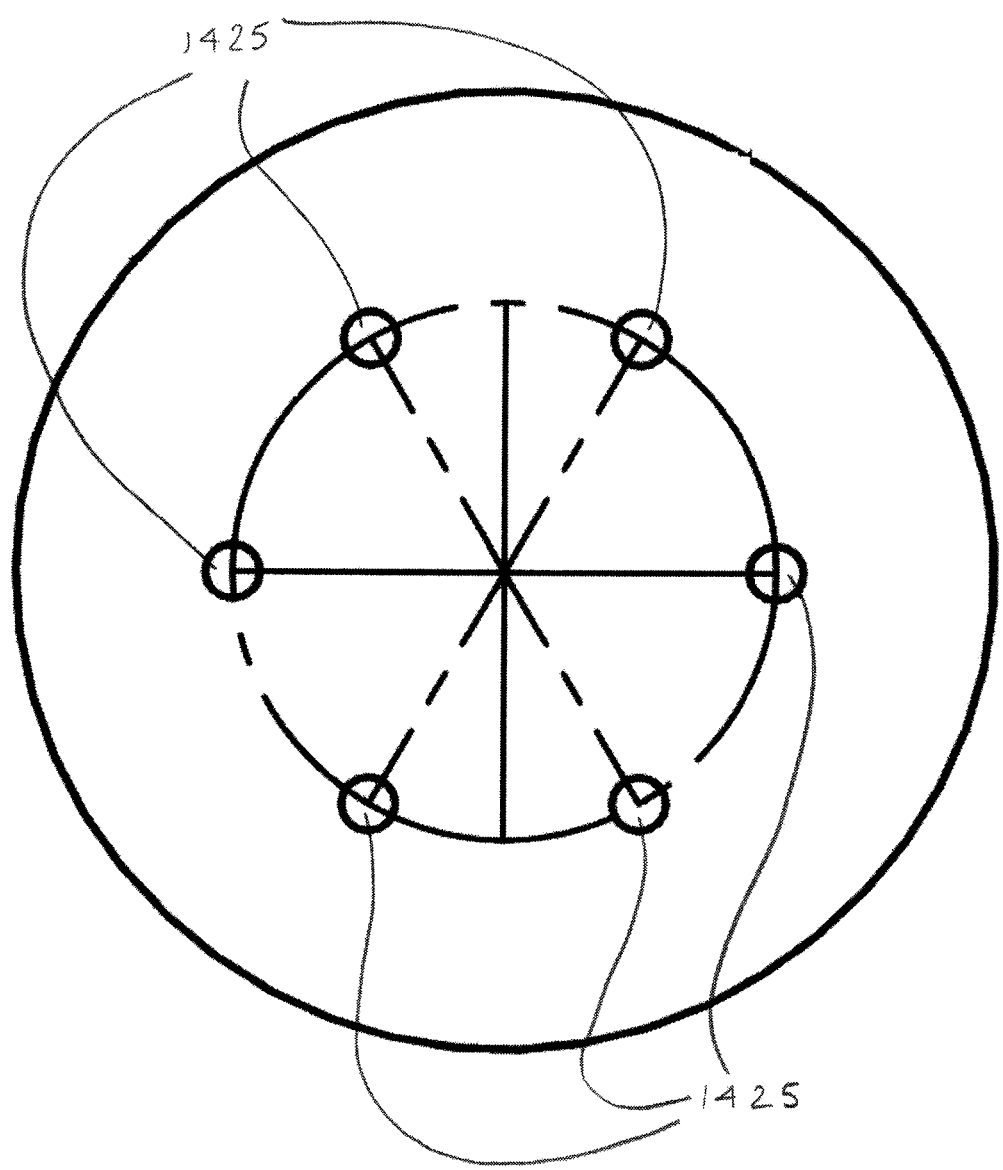
FIG. 17 is an enlarged view of a portion of the stator plate of FIG. 14.

FIG. 17 is an enlarged partial view of the detail of B from FIG. 14. In FIG. 17, the six openings 1425 are shown more clearly. Those skilled in the art will appreciate that more or less than six openings 1425 may be provided by the stator plate 1401.

Figure 18:
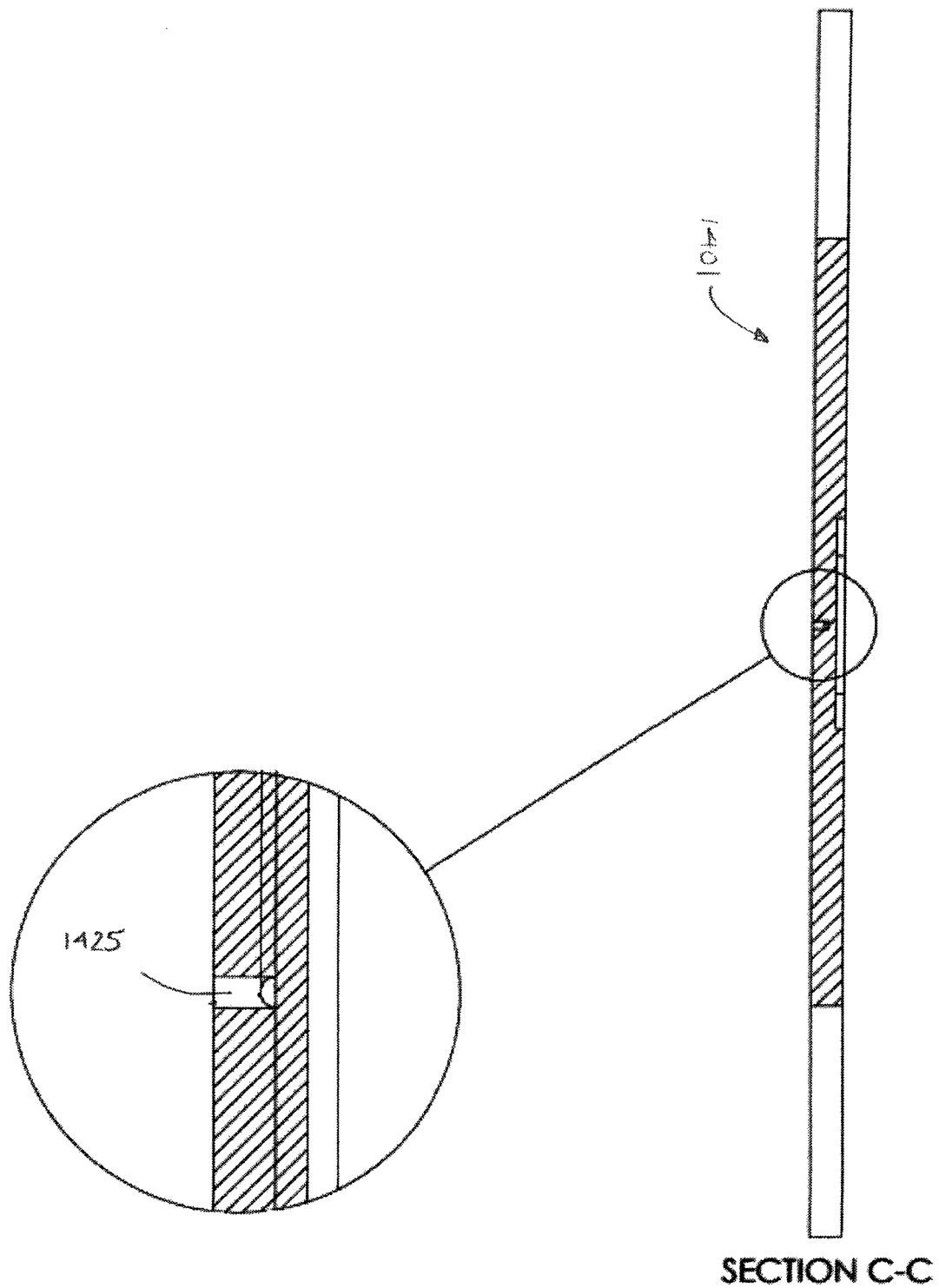
FIG. 18 is a cross-sectional view of the stator plate of FIG. 15 taken along line C-C and an enlarged portion thereof.

FIG. 18 provides another cross-sectional view of the stator plate 1401 along line C-C of FIG. 16. In addition, FIG. 18 provides an enlarged partial cross-sectional view of the opening 1425.

Referring now to FIGS. 19-23, additional views and details regarding a mounting device 1501 are provided. The same features in FIGS. 19-23 have the same reference numbers for ease of reference.

Figure 19:
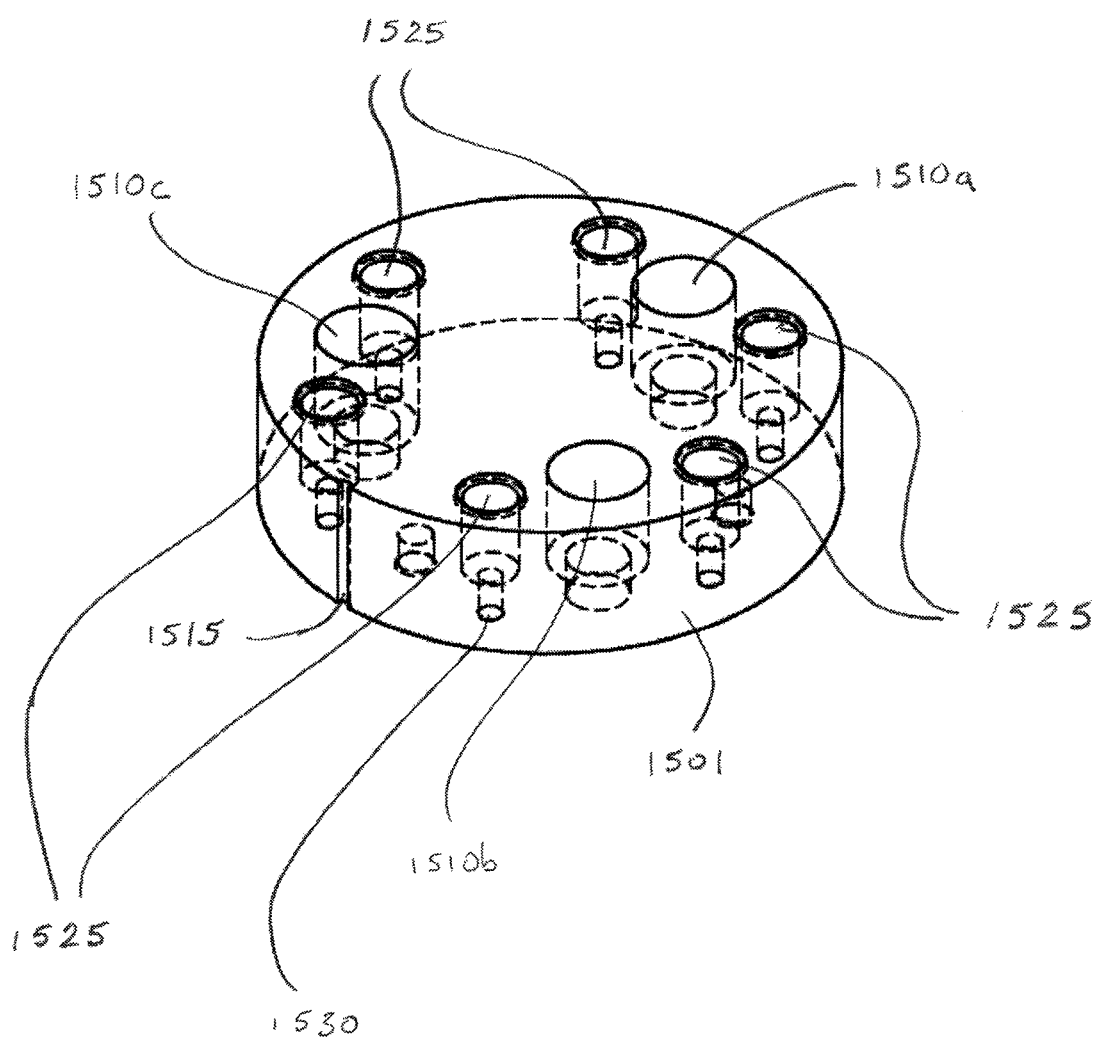
FIG. 19 is an isometric view of a mounting device in an embodiment in accordance with the present disclosure.

In FIG. 19, an isometric view of the mounting device 1501 is provided. Mounting device 1501 has six openings 1525, as well as three openings 1510a, 1510b, and 1510c. In addition, the mounting device 1501 has a groove or notch 1515 in its outer edge for easier and quicker alignment during assembly, with the groove 1515 running longitudinally along the outer edge of the mounting device 1501. It will be appreciated that the three openings 1510a, 1510b, and 1510c are each adapted to removably receive and hold a threaded screw or other fastener (not shown), so that the mounting device 1501 can be removably attached securely to a stator plate and to a valve body (not shown). In addition, it will be appreciated that each of the openings 1525 are adapted to removably receive tubing and a fitting assembly therein. In FIG. 19, the openings 1525 provide ports into which tubing and fitting assemblies may be inserted and securely connected.

Figure 20:
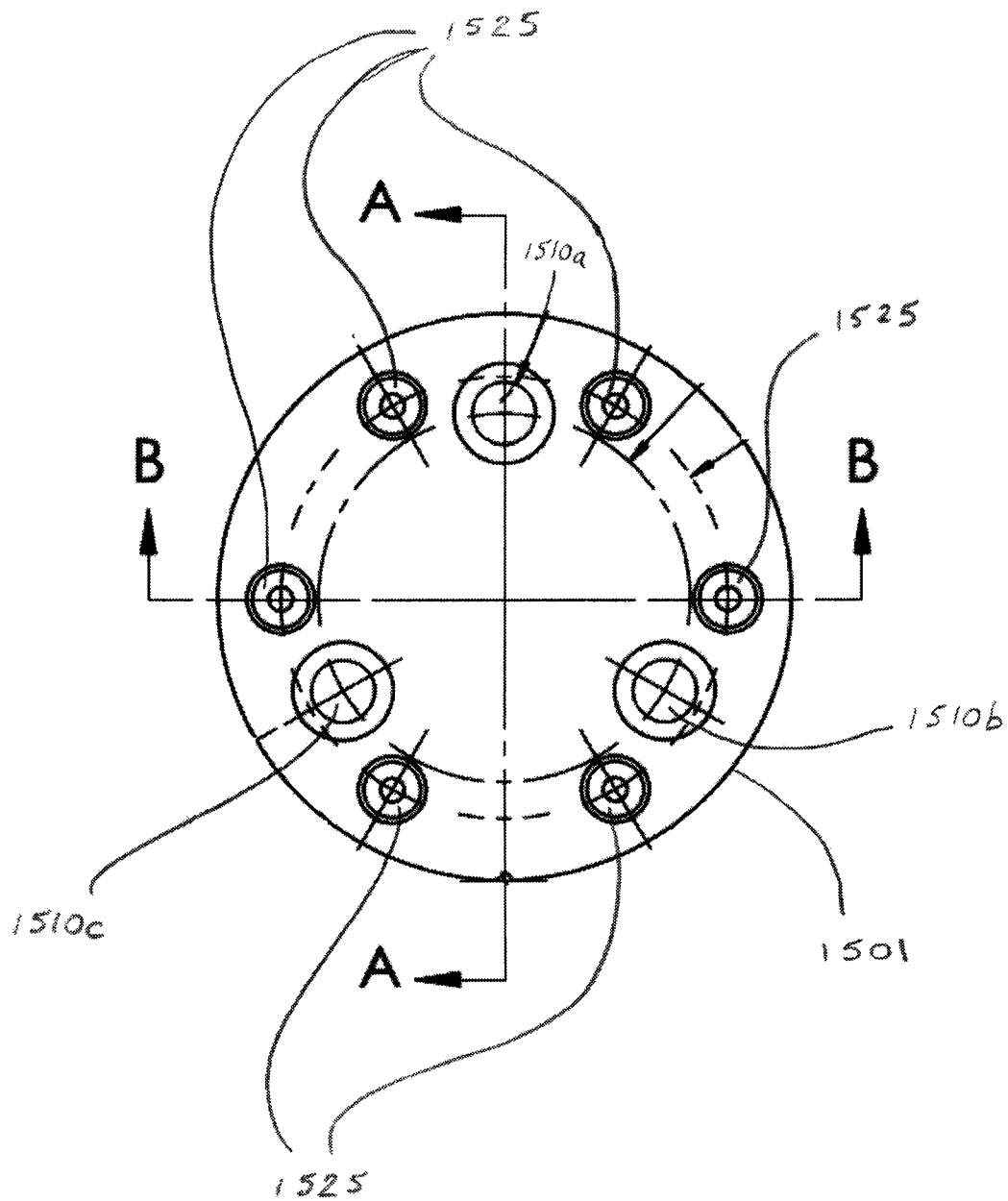
FIG. 20 is a top view of the mounting device of FIG. 19.

FIG. 20 is a top view of the mounting device 1501. Six openings or ports 1525 are shown, as are the three openings 1510a, 1510b, and 1510c for receiving threaded screws or fasteners. Those skilled in the art will appreciate that more or less than six ports 1525 may be provided, and that more or less than three openings for screws or other fasteners 1510a, 1510b, and 1510c may be provided.

Figure 21:
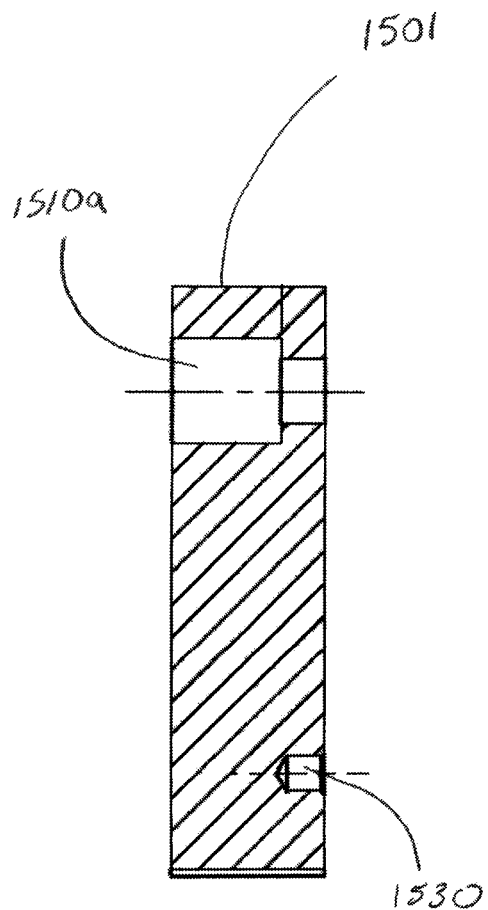
FIG. 21 is a cross-sectional view of the mounting device of FIG. 19 taken along line A-A of FIG. 20.

FIG. 21 is a cross-sectional view of the mounting device 1501 taken along line A-A of FIG. 20. The opening 1510a for receiving and holding a threaded screw or fastener is shown. Also shown is an opening 1530 on the bottom side of the mounting device 1501 to provide the positions for one of the locations pins (not shown). The opening 1530 is adapted to receive and removably hold the tip of one of the location pins (not shown).

Figure 22:
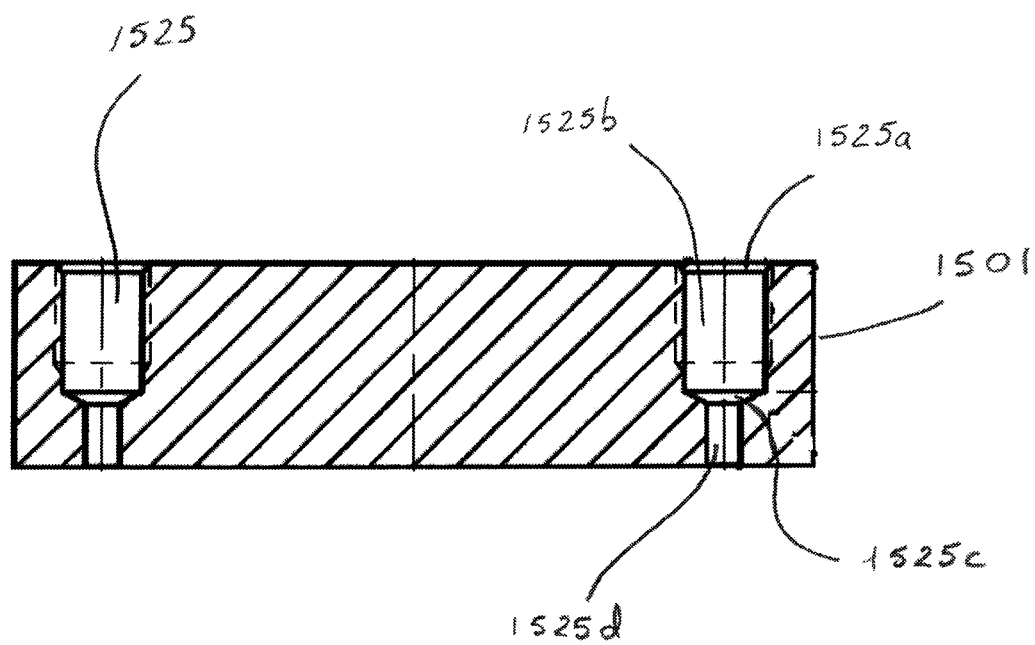
FIG. 22 is a cross-sectional view of the mounting device of FIG. 19 taken along line B-B of FIG. 20.

FIG. 22 is a cross-sectional view of the mounting device 1501 taken along line B-B of FIG. 20. In FIG. 22, two openings or ports 1525 are shown. The port 1525 on the right includes reference numerals to indicate the top portion 1525a, the middle portion 1525b, a guide portion 1525c, and a bottom portion 1525d of the port 1525 as it extends from the top of the mounting device 1501 to the bottom of the mounting device 1501.

Figure 23:
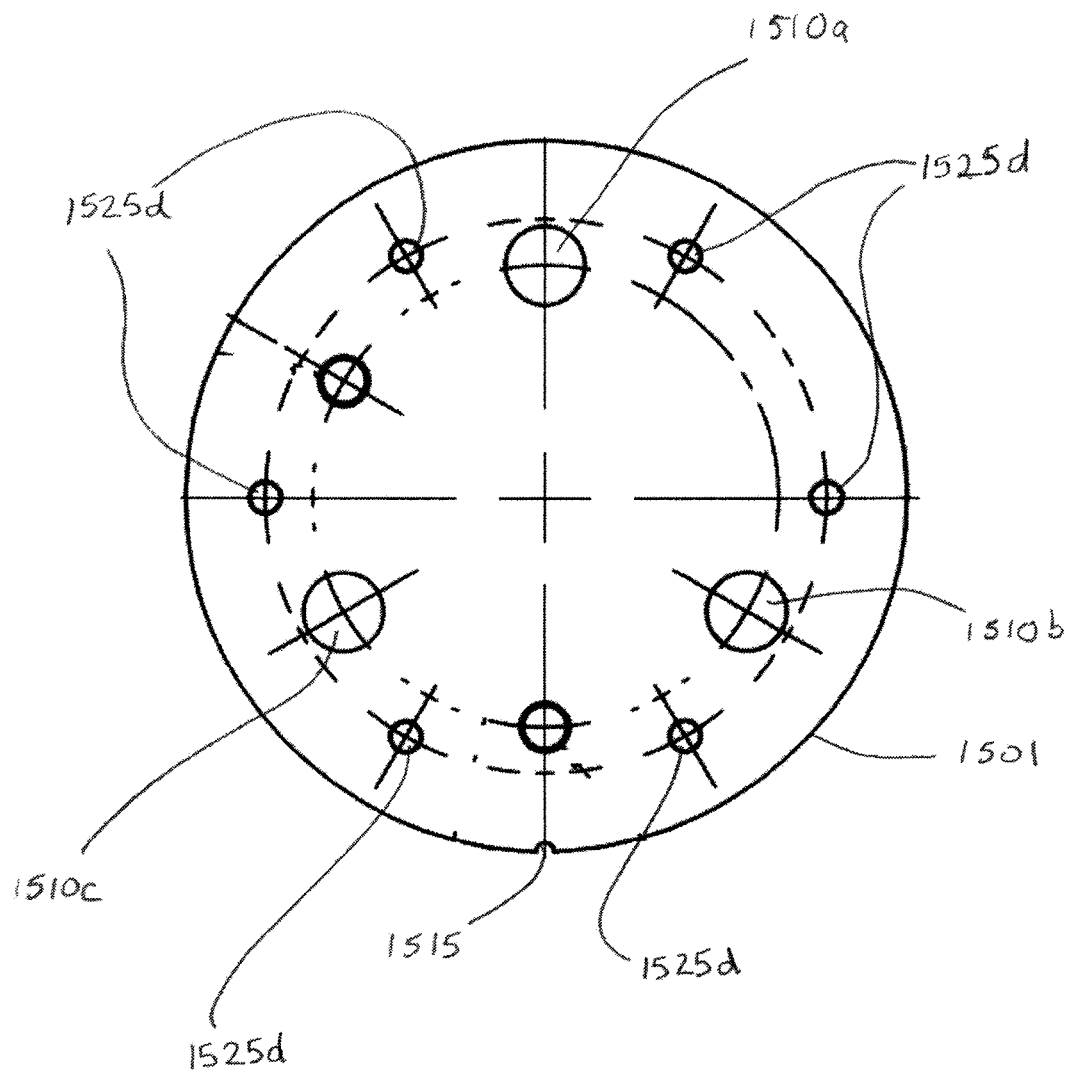
FIG. 23 is a bottom view of the mounting device of FIG. 19.

FIG. 23 provides a bottom view of the bottom face of the mounting device 1501. As shown in FIG. 23, openings 1510a, 1510b, and 1510c extend through the mounting device 1501. In addition, openings 1530 are provided on the bottom face of the mounting device 1501. Finally, the groove 1515 is also shown in FIG. 23.

Those skilled in the art will appreciate that a replaceable stator plate and a separate mounting device like those described above have several advantages over conventional valves. In addition, the mounting device of the present disclosure can be reduced in size from conventional stator heads for conventional valves, thus reducing costs of materials and also expensive machining operations to provide the flow passageways in conventional valves (which passageways are no longer needed with the two-piece assembly of the present disclosure). In addition, the openings of the mounting device can be aligned much more closely with the openings on the first side of the stator plate of the present disclosure, thereby reducing the potential for the introduction of turbulent flow and/or dead volume as is the case for conventional valves. At the same time, however, the openings of the stator plate and the passageways or grooves therein can be precisely controlled, such as to precisely control the volume of such passageways or grooves, which can be in the range of about 0.2 to about 0.6 microliters. Moreover, the valve of the present disclosure can be used even when the fluid flowing through the tubing and the valve is at high pressures, including pressures at anywhere from 5,000 psi to 30,000 psi or higher. Because the stator plate can comprise two or more layers which are bonded together, each of the layers can comprise one or more portions (such as grooves or channels) that are designed so that, when the two layers are bonded together, the portions align and fit together to form a passageway through the stator plate formed by the bonded layers. In addition, the optional use of the guide layer in the stator plate allows for a looser tolerance in terms of the alignment of the openings of the stator plate and the mounting device, thereby reducing cost and also providing a valve in which an operator can more easily and more quickly make and/or disassemble connections. The stator plate faces, including the fluid pathways (whether formed by grooves, passageways, or otherwise), can be coated (such as with a diamond-like carbon) if desired to reduce friction and increase hardness.

While the present invention has been shown and described in its preferred embodiment and in certain specific alternative embodiments, those skilled in the art will recognize from the foregoing discussion that various changes, modifications, and variations may be made thereto without departing from the spirit and scope of the invention as set forth in the claims. For example, those skilled in the art will appreciate that the foregoing description and figures generally depict a valve such as a rotary shear valve, but the foregoing disclosure applies to other types of valves as well. Hence, the embodiment and specific dimensions, materials and the like are merely illustrative and do not limit the scope of the invention or the claims herein.

We claim:

1. A high-pressure valve for liquid chromatography comprising:
   a mounting plate having a first side and a second side, and having a plurality of first openings therethrough, wherein each of the plurality of first openings is adapted to removably receive tubing in the first side of said mounting plate;
   a stator plate having a first side and a second side, wherein the first side of said stator plate is adapted to engage with the second side of said mounting plate, wherein said stator plate has a plurality of second openings in the first side of said stator plate, and a plurality of third openings in the second side of the stator plate, wherein the plurality of second openings define a first circle having a first diameter, the plurality of third openings define a second circle having a second diameter, the first diameter being greater than the second diameter, and wherein a plurality of fluid pathways extend between each of the plurality of the second openings and a corresponding one of each of the plurality of third openings;
   a rotor seal adapted to engage with at least one of the first side and second side of said stator plate;
   a rotor shaft which is rotatable around a longitudinal axis; and
   a housing within which the rotor seal and at least a portion of said rotor shaft are located, wherein said mounting plate and said stator plate are removably attached to said housing.

2. The valve according to claim 1 wherein said mounting plate comprises a first material and said stator plate comprises a second material.

3. The valve according to claim 2 wherein said stator plate comprises a biocompatible material.

4. The valve according to claim 1 wherein the plurality of openings in said mounting plate further comprise flat-bottom ports for removably receiving tubing.

5. The valve according to claim 4 wherein the first side of said stator plate further comprises bosses aligned to extend partially into the bottom of the first openings of said mounting plate.

6. The valve according to claim 1 wherein said stator plate comprises a plurality of layers bonded together.

7. The valve according to claim 6 wherein the plurality of layers bonded together comprise a plurality of layers bonded by diffusion bonding.

8. The valve according to claim 1 wherein said mounting plate comprises one or more of aluminum, copper, steel, stainless steel, titanium, polyetheretherketone, polypropylene, polysulfone, DELRIN, ULTEM, polyphenylen sulfide (PPS), polytetrafluoroethylene, nylon, polyamides, or a combination thereof.

9. The valve according to claim 1 wherein said stator plate comprises a plurality of layers bonded together, wherein at least one of said layers comprises one or more of stainless steel, titanium, MP35N, ceramics, glass, or a combination thereof.

10. The valve according to claim 1 wherein said stator plate further comprises a guide layer, wherein the guide layer comprises the plurality of second openings, each with a greater width than the third openings, and wherein the guide layer is adapted to be adjacent to the second side of said mounting plate.

11. The valve according to claim 1 wherein the stator plate and the mounting plate are removably attached to one another, and wherein said stator plate is adapted to be removable from said valve.

12. The valve according to claim 1 wherein said valve is adapted to operate with fluid pressures of a fluid flowing therethrough of at least 5,000 psi.

13. The valve according to claim 1 wherein said valve is adapted to operate with fluid pressures of a fluid flowing therethrough of at least 10,000 psi.

14. The valve according to claim 1 wherein said valve is adapted to operate with fluid pressures of a fluid flowing therethrough of at least 15,000 psi.

15. The valve according to claim 1 wherein said valve is adapted to operate with fluid pressures of a fluid flowing therethrough of at least 20,000 psi.

16. The valve according to claim 1 wherein said valve is adapted to operate with fluid pressures of a fluid flowing therethrough of at least 25,000 psi.

17. The valve according to claim 1 wherein the stator plate further comprises at least one of a sample loop, a mixing element, a column, a filter, a heating element, a sensor, and a detector.

18. The high-pressure valve according to claim 1 wherein the plurality of openings of the mounting plate are each adapted to removably receive a corresponding tubing assembly at an angle of between 80 and 100 degrees with respect to the transverse axis of the valve.

19. The valve according to claim 1 wherein the mounting plate and the stator plate are adapted to allow the tubing to be sealingly engaged with the first side of the stator plate.

20. The valve according to claim 1 wherein each of the plurality of first openings is adapted to removably receive tubing in the first side of said mounting plate at an angle of between 80 degrees and 100 degrees with respect to the transverse axis of the valve.

21. The valve according to claim 1 wherein each of plurality of the fluid pathways comprises a 90 degree bend.

22. A high-pressure valve for liquid chromatography comprising:
   a mounting plate having a first side and a second side, wherein the first side of the mounting plate comprises a plurality of ports, each having a fluid pathway to a corresponding one of a plurality of first openings in the second side of the mounting plate, wherein each of the plurality of ports is adapted to removably receive tubing;
   a stator plate having a first side and a second side, wherein the first side of the stator plate is adapted to engage with the second side of said mounting plate, wherein the stator plate has a plurality of second openings in the first side of the stator plate and a plurality of third openings in the second side of the stator plate, wherein a plurality of fluid pathways extend between each of the ports to one of the plurality of third openings, wherein said stator plate and said mounting plate are removably attached to one another, and wherein the mounting plate and the stator plate are adapted to allow the tubing to be sealingly engaged with the first side of the stator plate;

a rotor seal adapted to sealingly engage with the second side of the stator plate, wherein a first side of the rotor seal has at least one channel adapted to provide a fluid pathway between a plurality of the third openings;

a rotor shaft which is rotatable around a longitudinal axis; and a housing within which the rotor seal and at least a portion of said rotor shaft are located wherein said mounting plate and said stator plate are removably attached to said housing.

23. The valve according to claim 22 wherein said mounting plate comprises a first material and said stator plate comprises a second material.

24. The valve according to claim 22 wherein said stator plate comprises a biocompatible material.

25. The valve according to claim 22 wherein the stator plate comprises a guide layer defining the plurality of second openings, each having a greater width than the width of a corresponding one of the plurality of third openings, and wherein the first side of said stator plate further comprises bosses aligned to extend partially into the bottom of the ports of said mounting plate.

26. The valve according to claim 22 wherein said stator plate comprises a plurality of layers bonded together.

27. The valve according to claim 26 wherein the plurality of layers bonded together comprise a plurality of layers bonded by diffusion bonding.

28. The valve according to claim 22 wherein said mounting plate comprises one or more of aluminum, copper, steel, stainless steel, titanium, polyetheretherketone, polypropylene, polysulfone, DELRIN, ULTEM, polyphenylen sulfide (PPS), polytetrafluoroethylene, nylon, polyamides, or a combination thereof.

29. The valve according to claim 22 wherein said stator plate comprises a plurality of layers bonded together, wherein at least one of said layers comprises one or more of stainless steel, titanium, MP35N, ceramics, glass, or a combination thereof.

30. The valve according to claim 22 wherein said stator plate is adapted to be removable from said valve.

31. The valve according to claim 22 wherein said valve is adapted to operate with fluid pressures of a fluid flowing therethrough of at least 5,000 psi.

32. The valve according to claim 22 wherein said valve is adapted to operate with fluid pressures of a fluid flowing therethrough of at least 10,000 psi.

33. The valve according to claim 22 wherein said valve is adapted to operate with fluid pressures of a fluid flowing therethrough of at least 15,000 psi.

34. The valve according to claim 22 wherein said valve is adapted to operate with fluid pressures of a fluid flowing therethrough of at least 20,000 psi.

35. The valve according to claim 22 wherein said valve is adapted to operate with fluid pressures of a fluid flowing therethrough of at least 25,000 psi.

36. The valve according to claim 22 wherein each of the plurality of ports is adapted to removably receive tubing in the first side of said mounting plate at an angle of between 80 degrees and 100 degrees with respect to the transverse axis of the valve.

37. The valve according to claim 22 wherein the plurality of second openings define a first circle having a first diameter, and the plurality of third openings define a second circle having a second diameter, the first diameter being greater than the second diameter, and wherein the plurality of fluid pathways extend between each of the plurality of the second openings and a corresponding one of each of the plurality of third openings.

38. The valve according to claim 22 wherein each of the plurality of fluid pathways comprises a 90 degree bend.

* * * * *